United States Patent [19]

Cerny et al.

[11] Patent Number: 5,437,603
[45] Date of Patent: Aug. 1, 1995

[54] APPARATUS AND METHOD FOR IMPLANTING PROSTHESES WITHIN PERIURETHRAL TISSUES

[75] Inventors: David E. Cerny, Lilburn, Ga.; Christopher J. Brooks, Glen Head, N.Y.

[73] Assignee: C.R. Bard, Inc., Murray Hill, N.J.

[21] Appl. No.: 120,943

[22] Filed: Sep. 14, 1993

[51] Int. Cl.$^6$ .................................................. A61F 2/00
[52] U.S. Cl. ............................. 600/29; 128/DIG. 25
[58] Field of Search .................................. 600/29-32; 128/DIG. 25: 897-899

[56] References Cited

U.S. PATENT DOCUMENTS

| | | |
|---|---|---|
| 2,245,350 | 6/1941 | Marshall . |
| 2,513,014 | 6/1950 | Fields . |
| 2,712,314 | 7/1955 | Kohl . |
| 2,898,785 | 8/1959 | Quick et al. . |
| 2,996,936 | 8/1961 | Blaise . |
| 3,016,895 | 1/1962 | Sein . |
| 3,016,899 | 1/1962 | Stenvall . |
| 4,240,433 | 12/1980 | Bordow . |
| 4,686,962 | 8/1987 | Haber . |
| 4,773,393 | 9/1988 | Haber et al. . |
| 4,799,921 | 1/1989 | Johnson et al. . |
| 4,802,479 | 2/1989 | Haber et al. . |
| 4,832,680 | 5/1989 | Haber et al. . |

Primary Examiner—William E. Kamm
Assistant Examiner—John P. Lacyk
Attorney, Agent, or Firm—Jones & Askew

[57] ABSTRACT

An apparatus is disclosed for guiding a medical instrument to a predetermined target location within the periurethral tissues of a patient. The apparatus directs the instrument along a predetermined path with respect to the patient's urethra and limits penetration of the instrument to a predetermined depth. The disclosed embodiment comprises an apparatus for implanting inflatable prostheses within the periurethral tissues to coapt the urethra and thereby manage incontinence. A method for effecting coaptation of a urethra of a patient is also disclosed. According to this method, a pair of working channels are formed within the periurethral tissues, and an inflatable prosthesis is introduced into each working channel. The prostheses are inflated only after both working channels have been formed, and preferably after both prostheses have been positioned within their respective working channels. The inflated prostheses confront the urethra and effect coaptation of the urethra.

5 Claims, 19 Drawing Sheets

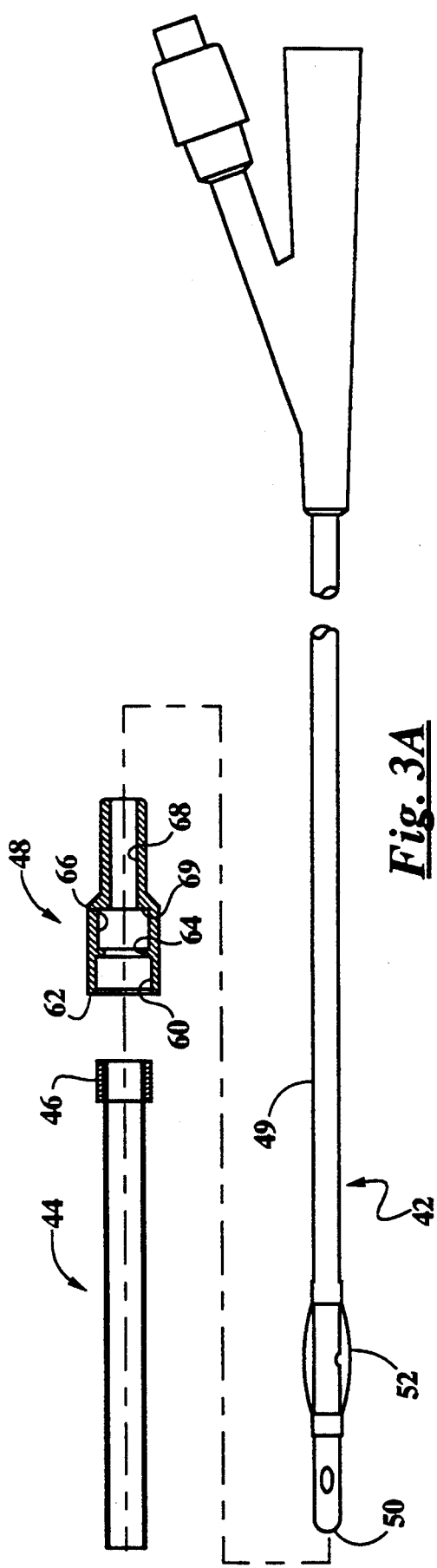
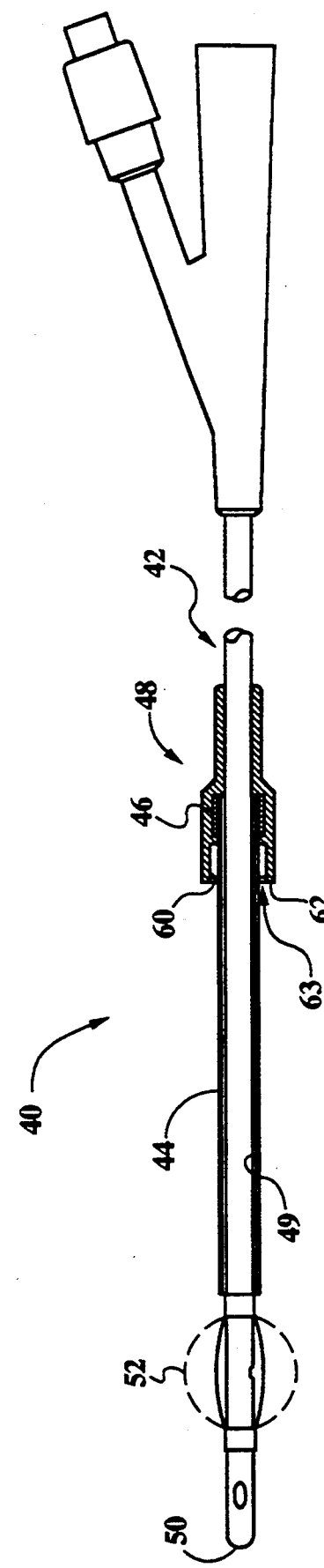

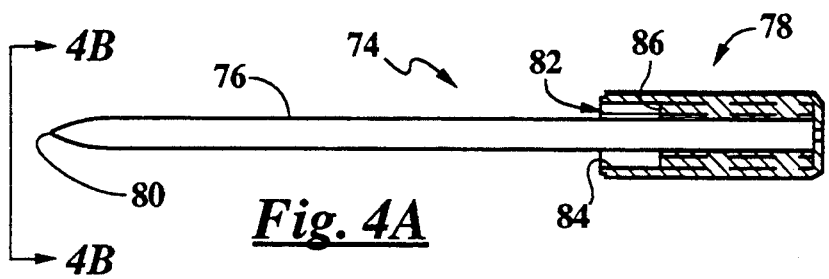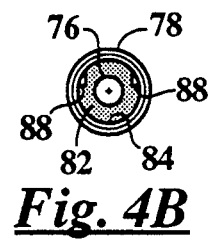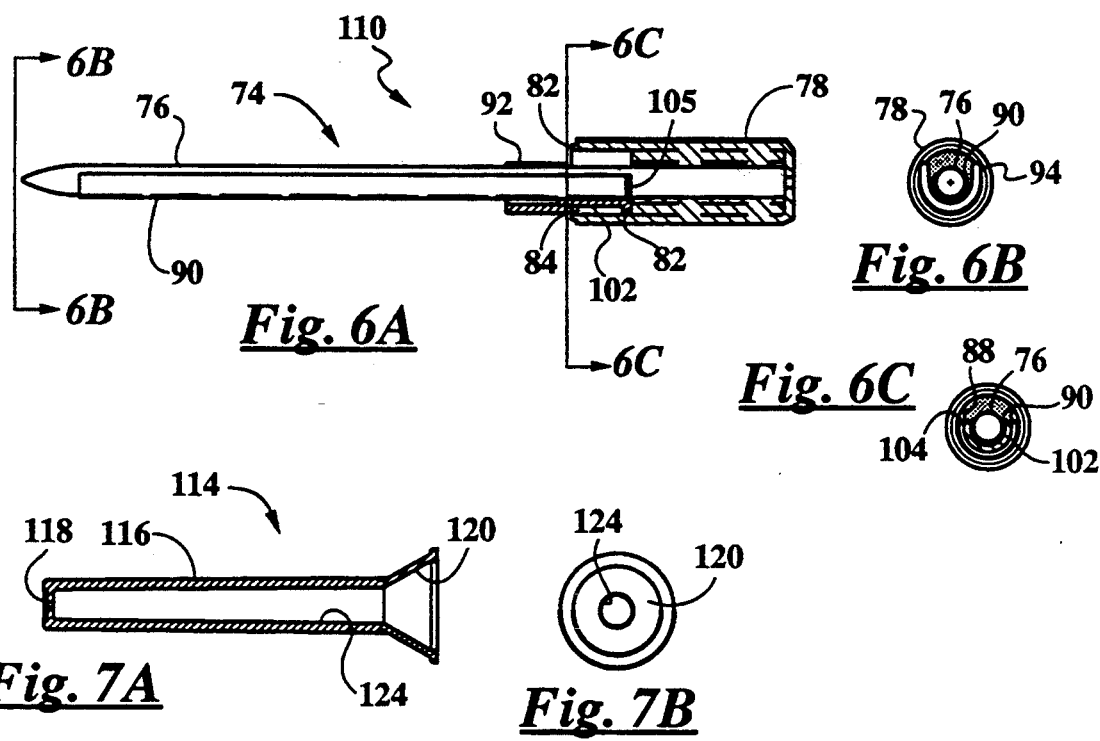

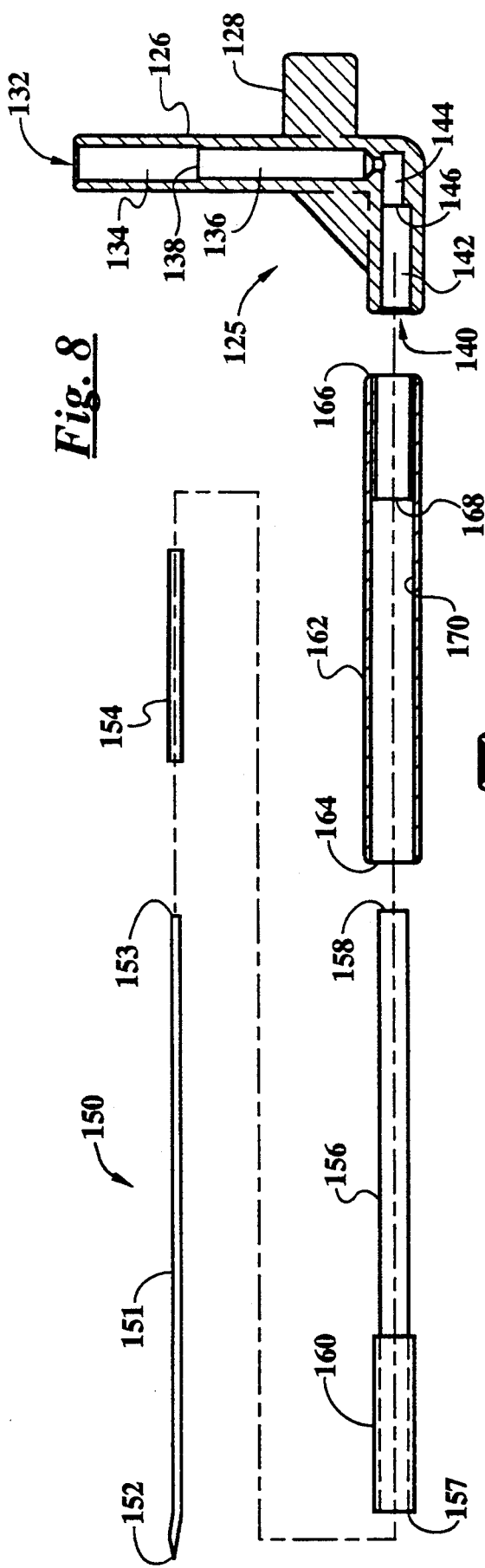
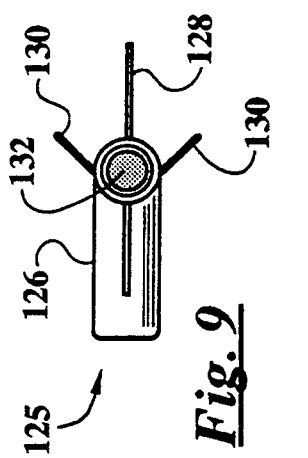
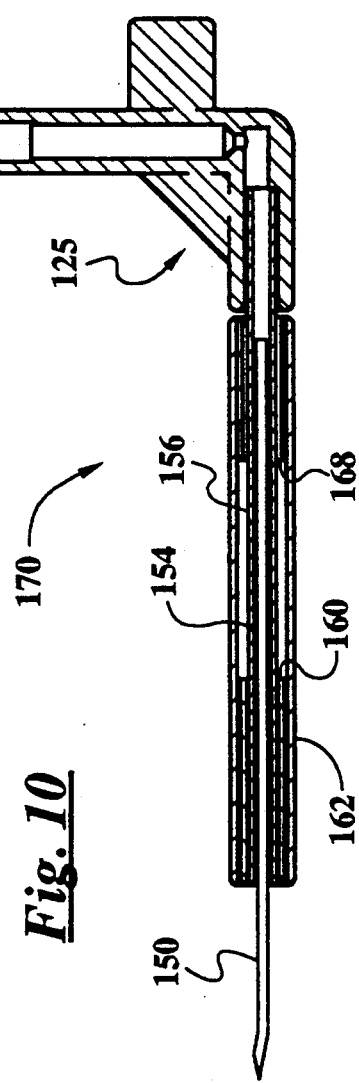
Fig. 8
Fig. 9
Fig. 10

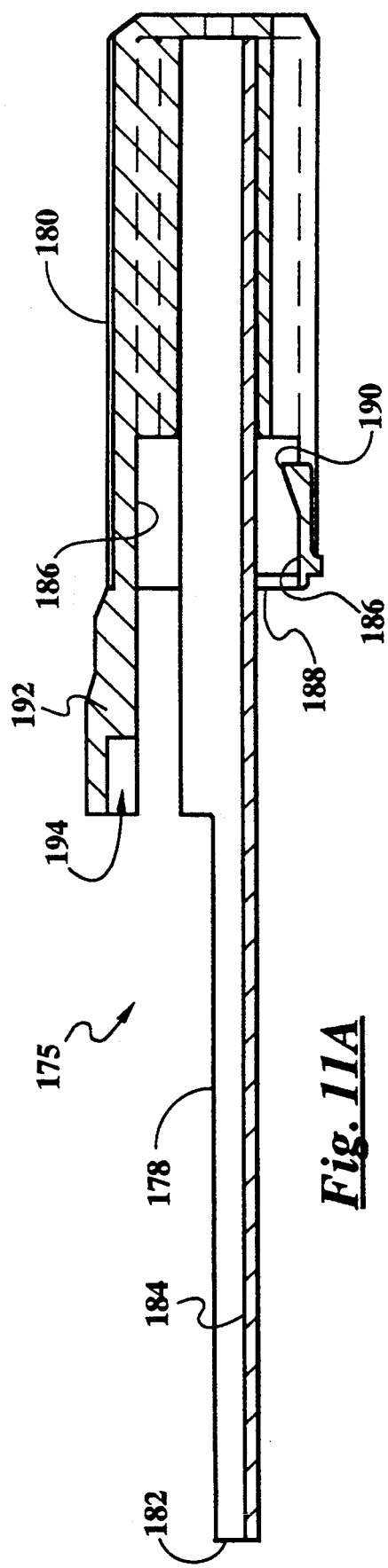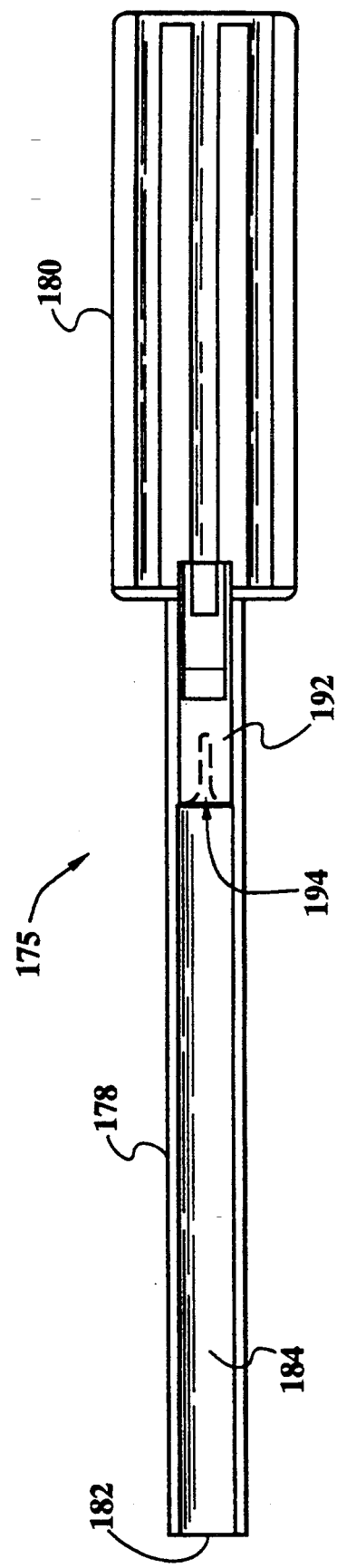
Fig. 11A
Fig. 11B

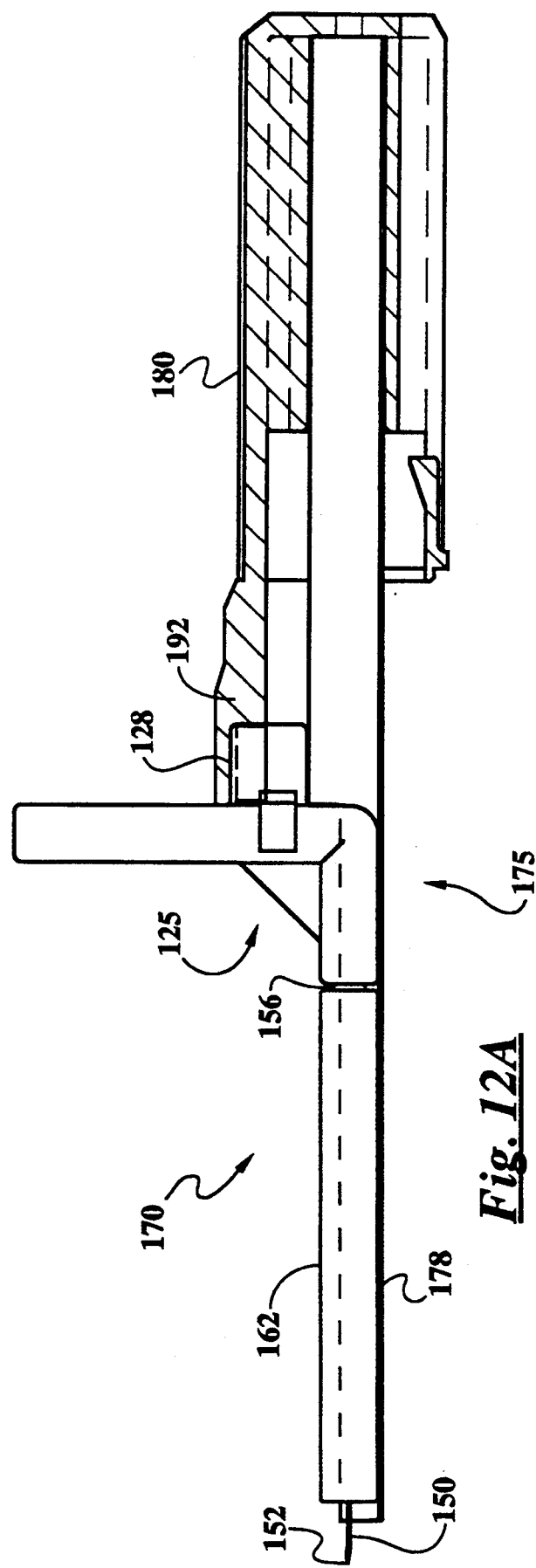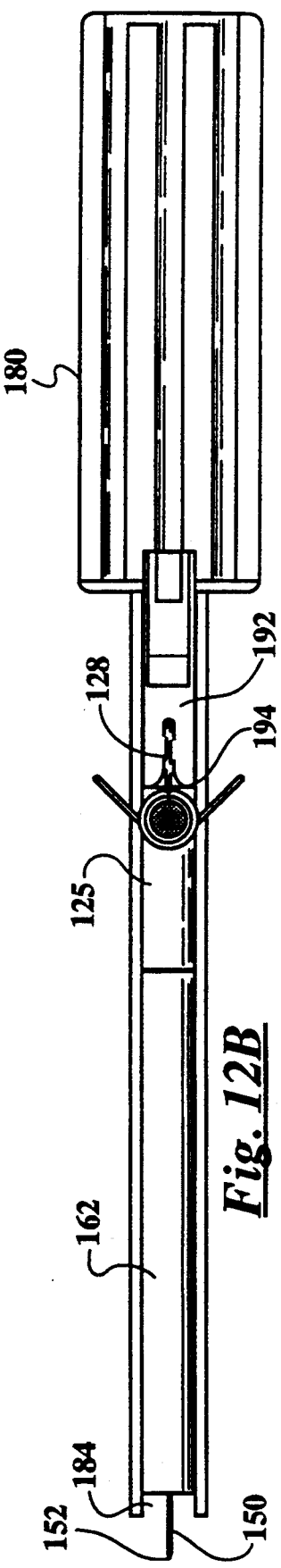

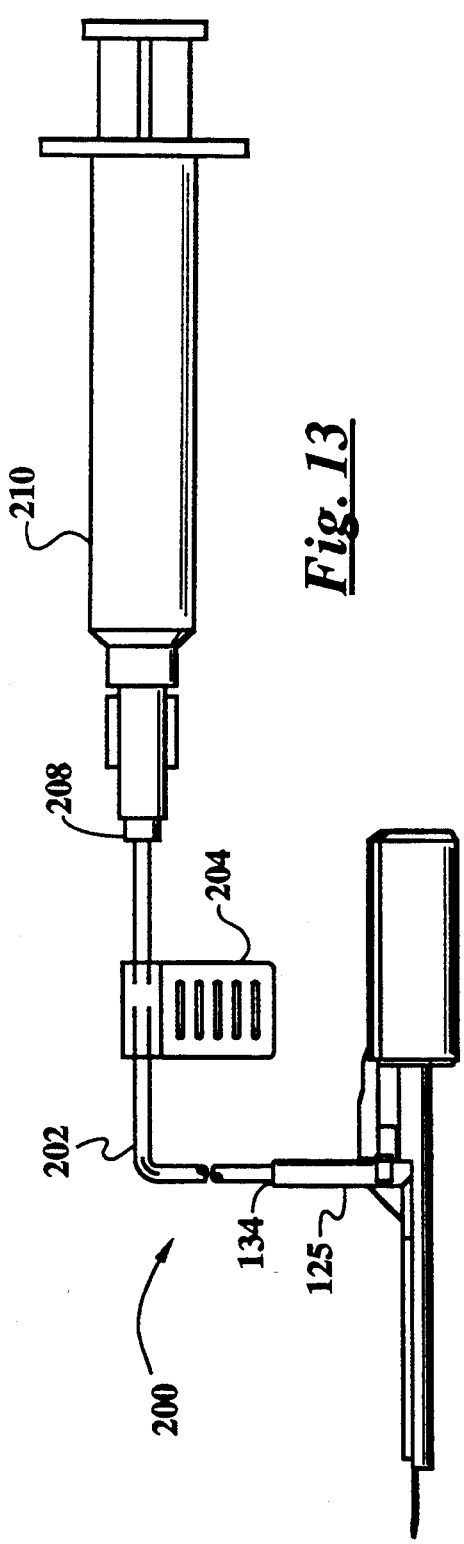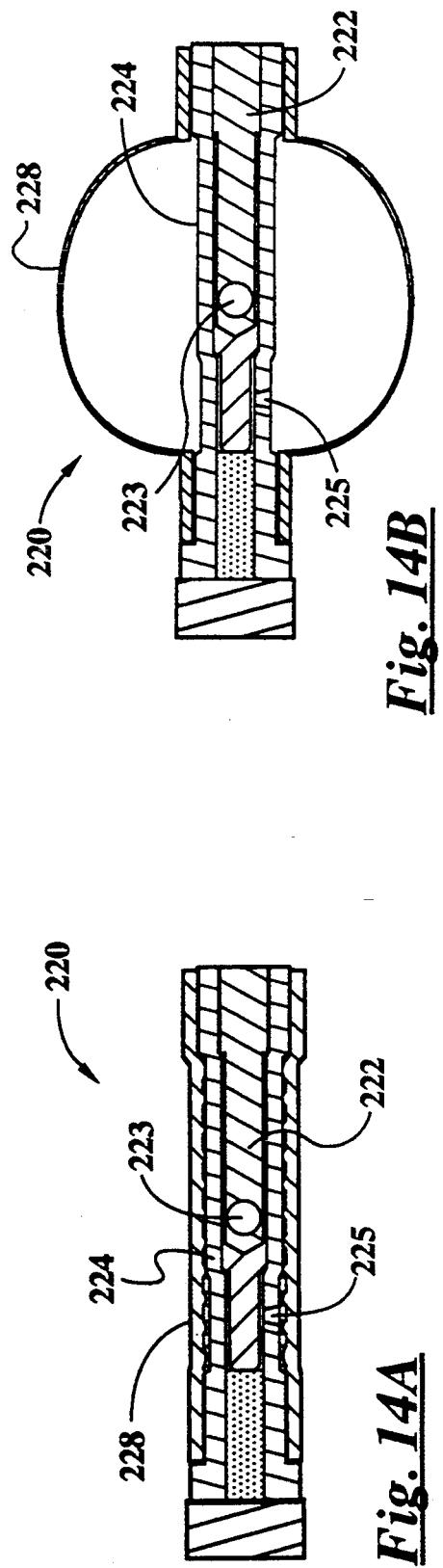

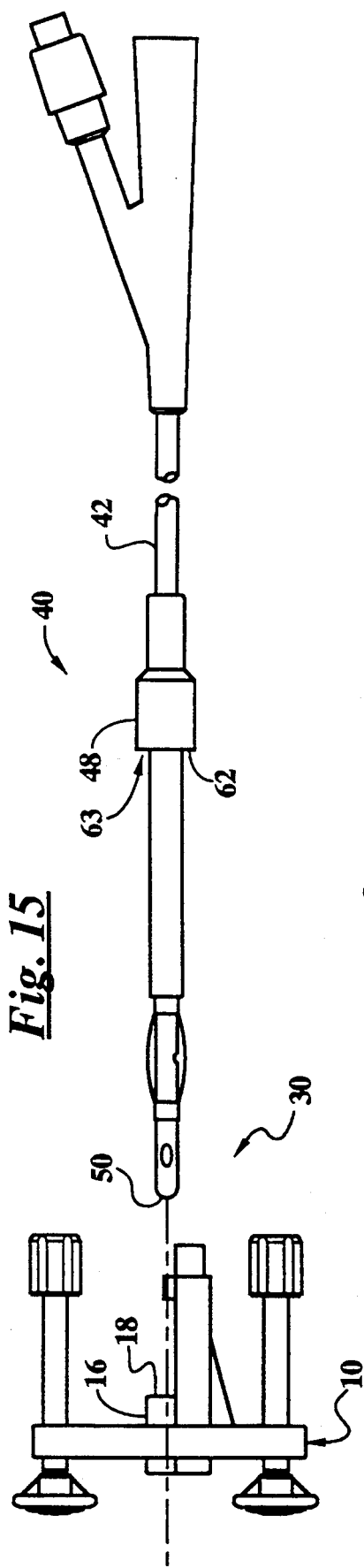
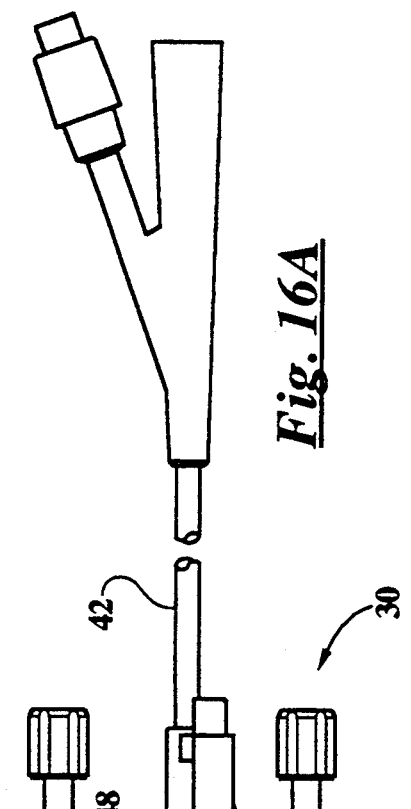
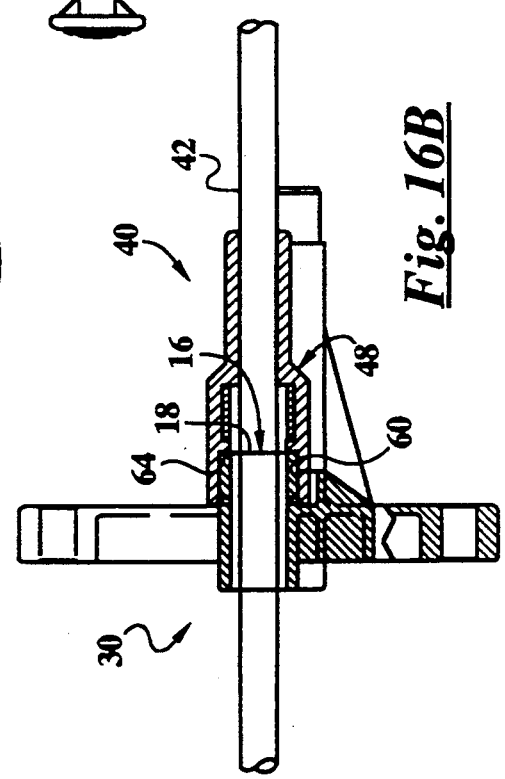

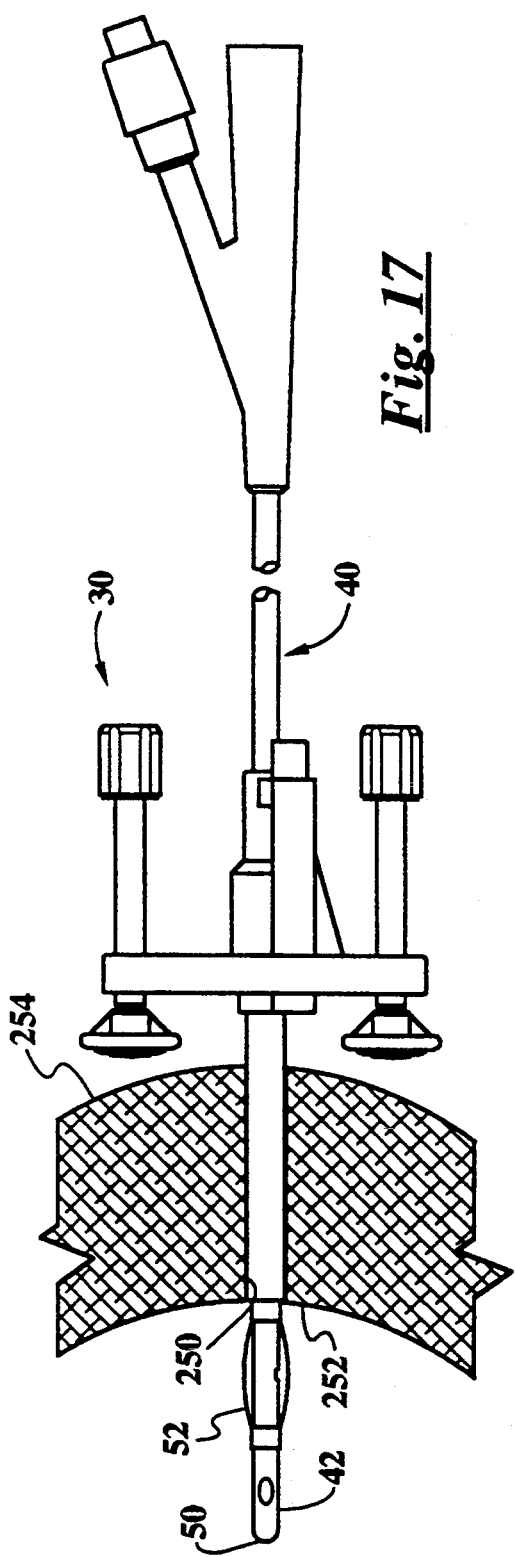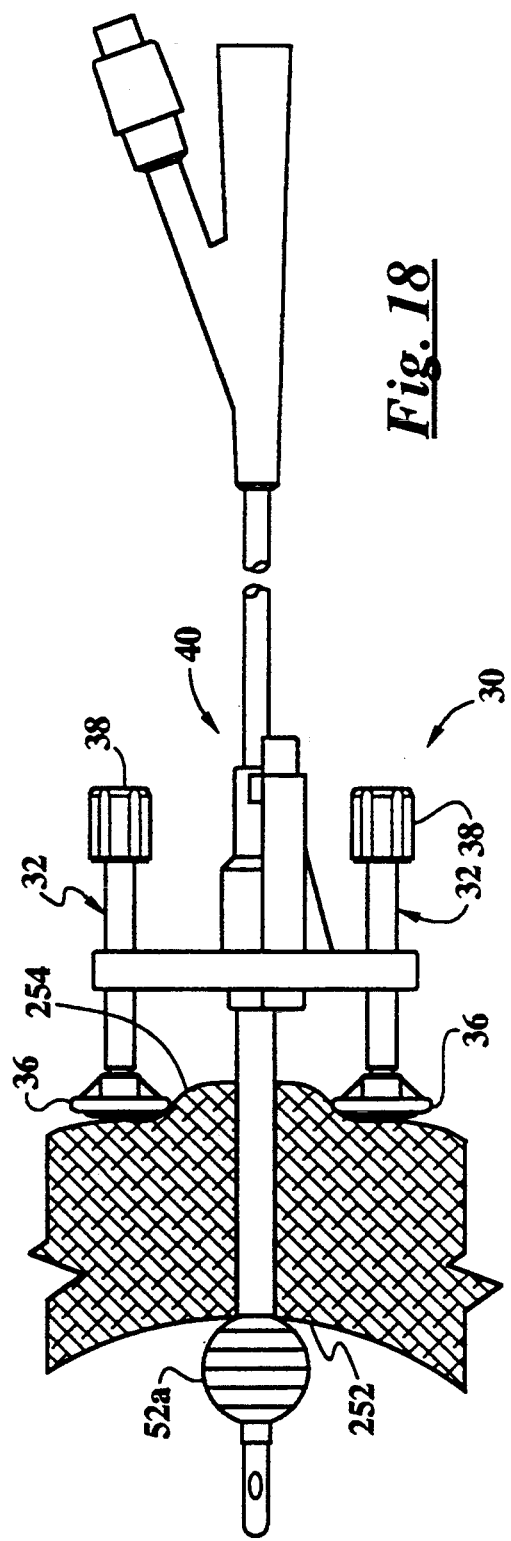

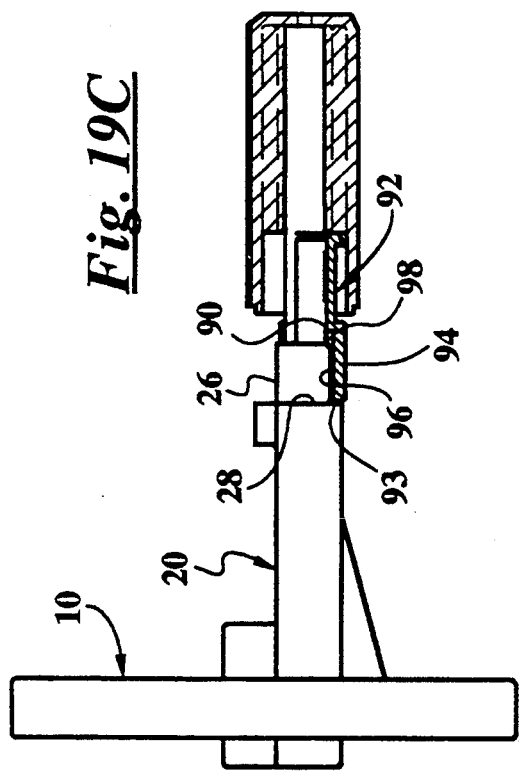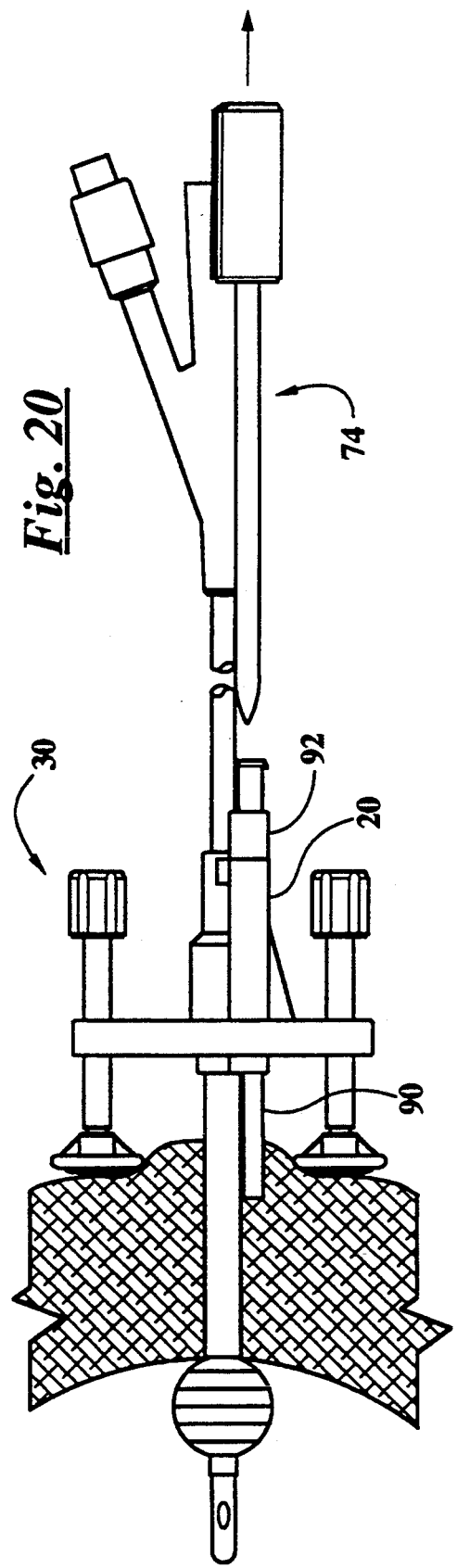

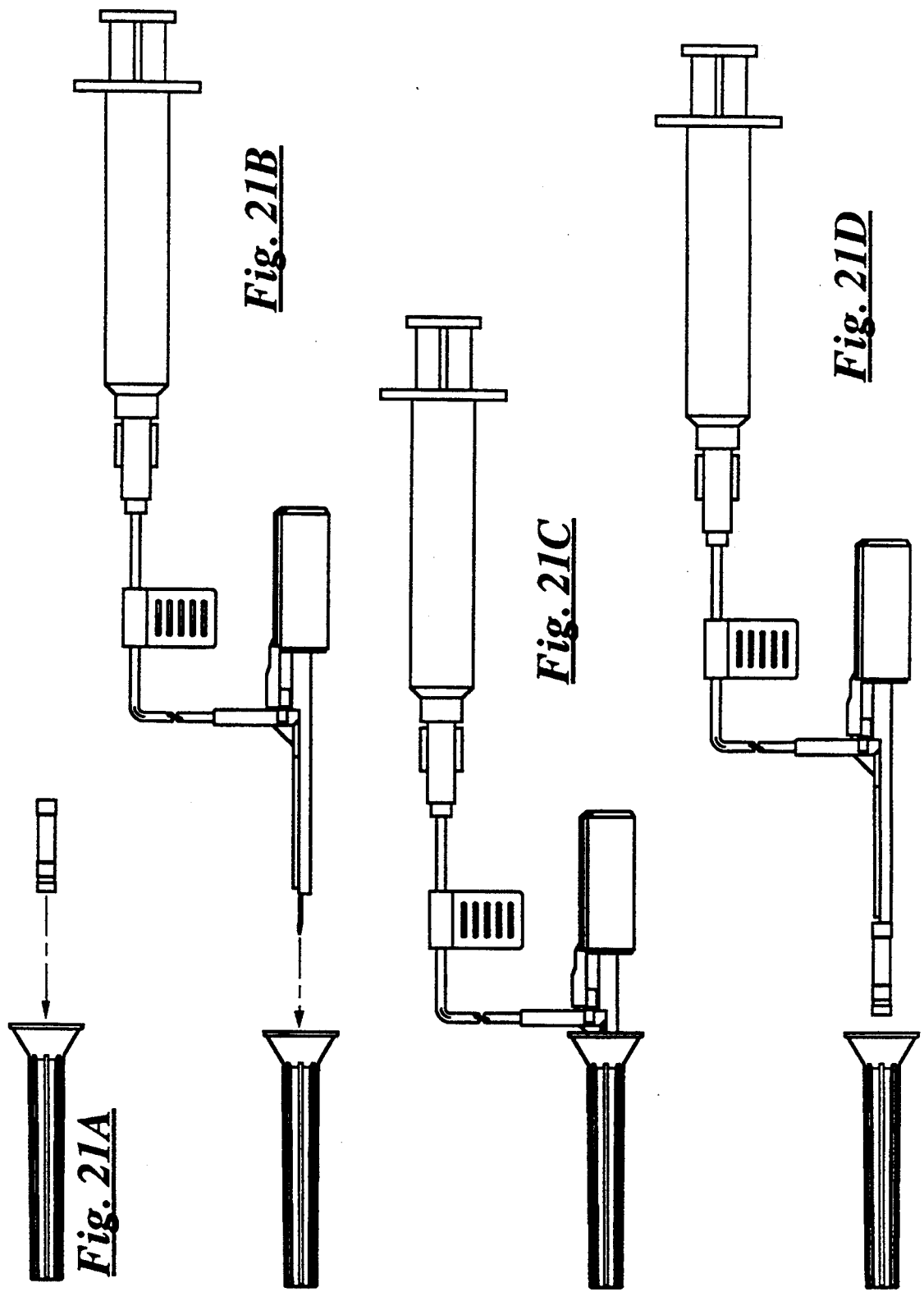

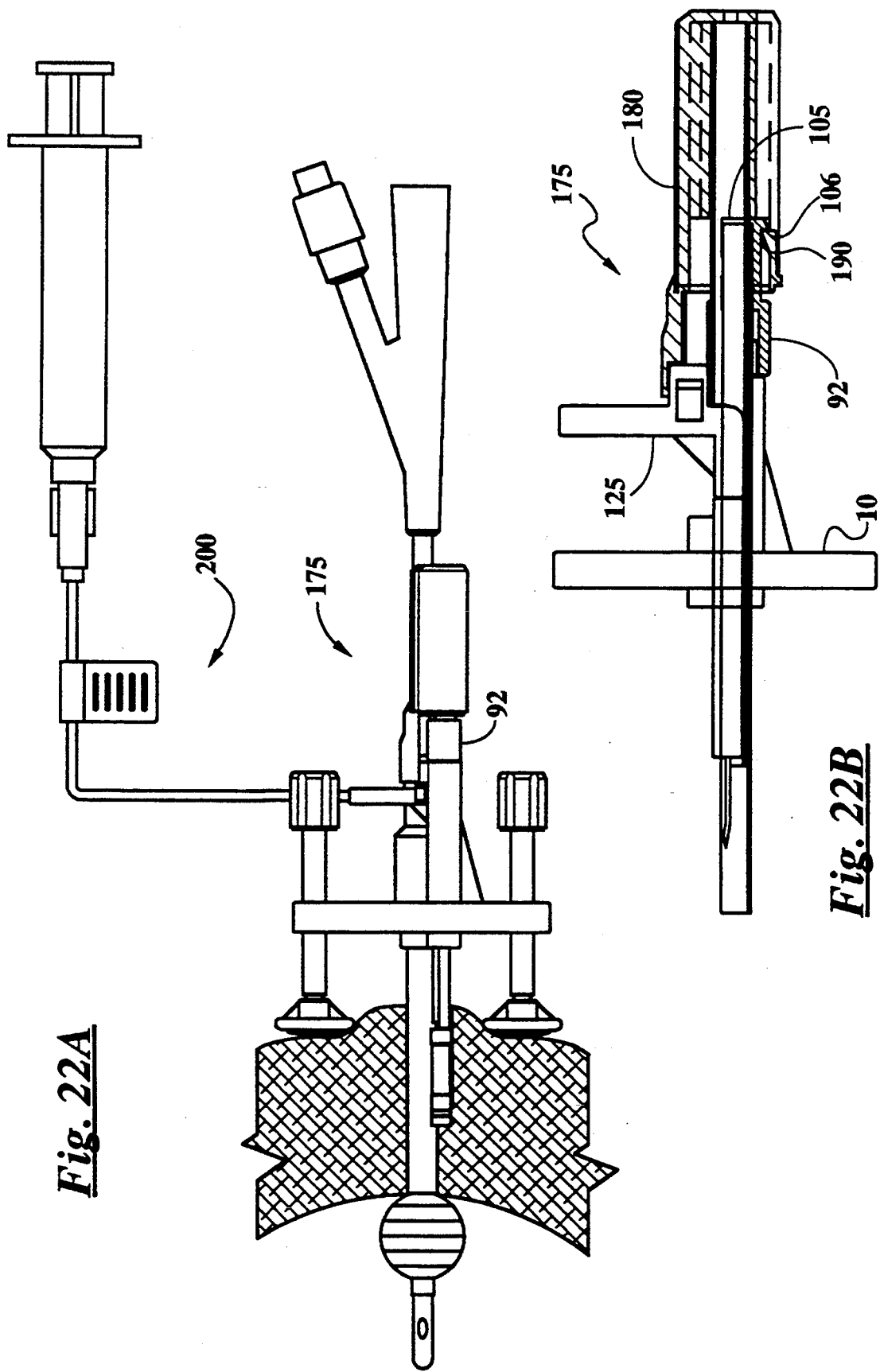

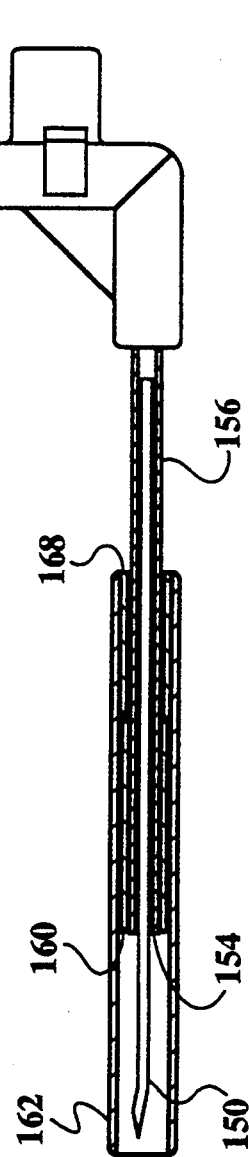
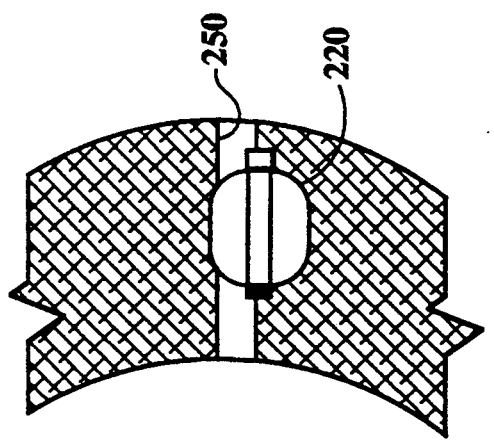
*Fig. 27A*
*Fig. 27B*

APPARATUS AND METHOD FOR IMPLANTING PROSTHESES WITHIN PERIURETHRAL TISSUES

TECHNICAL FIELD

The present invention relates generally to medical devices and procedures. More specifically the present invention relates to an apparatus for directing a hypodermic instrument to a predetermined target location within the periurethral tissues and to an apparatus and method for implanting a device or injecting a substance at a predetermined target location within the periurethral tissues.

BACKGROUND OF THE INVENTION

It is known to treat stress urinary incontinence by implanting an inflatable prosthesis within the periurethral tissues. When the prosthesis is properly positioned within the periurethral tissues and inflated, localized tissue volume is increased, enhancing the passive occlusive pressure of the urethral sphincter and thereby achieving continence. Examples of such inflatable prostheses and of instruments for implanting, dispensing, and inflating these prostheses in the periurethral tissues are shown, for example, in U.S. Pat. Nos. 4,686,962, 4,773,393, 4,802,479, and 4,832,680, which patents are incorporated herein by reference.

Prior art procedures for implanting the inflatable prosthesis in the periurethral tissues comprise forming a first trocar tract to the periurethral tissues on one side of the sphincter. A prosthesis is placed on the tip of a catheter and introduced through this tract to a target location within the periurethral tissues. An isotonic fluid medium is then infused through the catheter and into the prosthesis to inflate it. A second trocar tract is then formed to the periurethral tissues on the other side of the sphincter, and the procedure is repeated with a second prosthesis through the other trocar tract.

Certain difficulties are presented by these prior art implantation procedures. For example, it can be difficult to position the implants properly along the length of the urethra so as to be properly positioned with respect to the sphincter. If the prosthetic devices are not properly positioned with respect to the urethral sphincter, the occlusive pressure will be suboptimal, and continence may not be achieved. Also, the possibility exists that the physician could accidentally puncture the urethra or bladder while implanting the devices. Further, since the trocar tracts are formed independently, the inflation of the first implant can distend the periurethral tissues and push the urethra away from its normal alignment, thereby making the proper positioning of the second implant more difficult.

Finally, the prior art procedure can be somewhat difficult for the physician to perform and may require more than one attempt to properly position the implants, thereby resulting in increased trauma to the patient.

Thus there is a need for an improved apparatus and method for implanting prostheses within periurethral tissues.

There is also a need for an apparatus and method for implanting prostheses within periurethral tissues which will ensure proper positioning of the implants with respect to the urethral sphincter.

Further there is a need for an apparatus and method for implanting prostheses within periurethral tissues which will prevent the possibility of the physician accidentally puncturing the urethra or bladder.

There exists a still further need for an apparatus and method for implanting a pair of prostheses within periurethral tissues in which the implantation of the first prosthesis does not adversely impact the physician's ability to position the second prosthesis properly.

SUMMARY OF THE INVENTION

As will be seen, the present invention overcomes these and other problems associated with prior art methods and delivery instruments for implanting inflatable implants in the periurethral tissues. Stated generally, the present invention comprises an apparatus and method for implanting prostheses within periurethral tissues which ensures proper positioning of the implants with respect to the urethral sphincter. The apparatus and method positively controls the depth and direction of implantation to reduce or eliminate the possibility of accidental puncture or laceration of the urethra or bladder. Furthermore the apparatus and method permit a pair of prostheses to be implanted within periurethral tissues without implantation of the first prosthesis adversely impacting the physician's ability to position the second prosthesis properly.

Stated somewhat more specifically, in a first aspect the present invention comprises an apparatus for guiding a tool along a path in predetermined relation with respect to the urethra of a patient. The apparatus comprises a catheter insertable into the urethra of a patient for placing the urethra in predetermined alignment. A template is operatively associated with the catheter and includes a guide means for directing a tool along a path in predetermined relation to the predetermined alignment. The guide means is operative to direct the tool along the path in predetermined relation with respect to the urethra of the patient.

In a second aspect, the present invention comprises an apparatus for guiding a tool to a predetermined depth with respect to the bladder neck of a patient. The apparatus comprises a catheter having an elongated shaft and being insertable into the urethra of a patient. The catheter comprises an engagement means disposed thereon operative upon the engagement means being introduced into the bladder of the patient for engaging the bladder neck of the patient. A template is operatively associated with the shaft of the catheter at a location in predetermined spaced apart relation to the engagement means of the catheter, whereby when the engagement means engages the bladder neck of the patient the template is located in predetermined location with respect to the bladder neck. The template includes a guide means for directing a tool along a predetermined path, and also includes stop means operatively associated with the guide means for limiting the extent of tool travel along the predetermined path. In this manner, when a tool is directed along the predetermined path and advanced until limited by the stop means, the tool is guided to a predetermined depth with respect to the bladder neck of the patient.

In yet a third aspect, the present invention comprises an apparatus for placing inflatable prostheses within the periurethral tissues of a patient. A template includes first, second, and third guide sleeves having first, second, and third axes respectively, the first and second axes being disposed in predetermined relation to the third axis. The template further includes stop means operatively associated with the first and second guide sleeves. A catheter is inserted through the third guide sleeve of the template and into the urethra of the patient. A balloon adjacent the forward end of the catheter is selectively inflatable when the catheter is inserted into the urethra of the patient to engage the bladder neck of the patient. A catheter stop means operatively associated with the catheter engages the template to locate the template at a location along the catheter in predetermined spaced relation to the balloon. In this manner the template is placed both in predetermined axial alignment with the urethra of the patient and in predetermined spaced relation from the bladder neck of the patient.

A working channel means is inserted through each of the first and second guide sleeves of the template for forming a pair of working channels within the periurethral tissues of the template. Each working channel means includes a stop means which limits the extent of travel of the working channel means with respect to the template such that the working channels are formed to a predetermined depth with respect to the template. A cannula means is then inserted through each of the first and second guide sleeves of the template for introducing an inflatable prosthesis through each working channel. The cannula means is also selectively operable to inflate the inflatable prostheses with a suitable medium. The cannula means includes engagement means for engaging the template so as to limit the depth to which the inflatable prostheses are introduced through the respective working channels. The engagement means also selectively releasably couples the first cannula means to the template.

In still a fourth aspect, the present invention comprises a method for effecting coaptation of a urethra of a patient. A first working channel is formed through the periurethral tissues of the patient to a first target location in predetermined relation to the urethra. A second working channel is then formed through the periurethral tissues of the patient to a second target location in predetermined relation to the urethra and to the first target location. Next, an inflatable prosthesis is inserted through the first working channel to the first target location; and another inflatable prosthesis through the second working channel to the second target location. After both working channels have been formed, the prostheses are inflated such that coaptation of the urethra results.

Thus it is an object of the present invention to provide an improved apparatus and method for implanting prostheses within periurethral tissues.

It is another object of the present invention to provide an improved apparatus and method for directing a hypodermic instrument to a predetermined target location within the periurethral tissues.

A further object of the present invention is to provide an apparatus and method for implanting prostheses within periurethral tissues which will ensure proper positioning of the implants with respect to the urethral sphincter.

Still another object of the present invention is to provide an apparatus and method for implanting prostheses within periurethral tissues which will prevent the possibility of the physician accidentally puncturing the urethra or bladder.

It is yet another object of the present invention to provide an apparatus and method for implanting a pair of prostheses within periurethral tissues in which the implantation of the first prosthesis does not adversely impact the physician's ability to position the second prosthesis accurately.

Other objects, features, and advantages of the present invention will become apparent upon reading the following specification, when taken in conjunction with the drawings and the appended claims.

BRIEF DESCRIPTION OF THE DRAWINGS

The apparatus of the disclosed embodiment is shown in FIGS. 1-14, where:

FIG. 1A is a back view of the template, FIG. 1B is a side cut-away view of the template along line 1B—1B of FIGS. 1A, 1C is a front view of the template, FIG. 1D is a side cut-away view of the template along line 1D—1D of FIGS. 1C, and 1E is a top view of the template.

FIG. 3A is an exploded side view of a catheter assembly comprising a component of the preferred embodiment of the apparatus of the present invention, with some subcomponents of the catheter assembly cut away to reveal interior detail; FIG. 3B is a side view of the catheter assembly of FIG. 3A assembled with some subcomponents cut away to reveal interior detail.

FIG. 4A is a side cut-away view of a trocar punch comprising a component of the apparatus of the preferred embodiment; FIG. 4B is an end view of the trocar punch along line 4B—4B of FIG. 4A.

FIG. 5A is a side view of a trocar outer sleeve comprising a component of the apparatus of the preferred embodiment; FIG. 5B is a partial side cutaway view of the trocar outer sleeve of FIGS. 5A; and 5C is an end view of the trocar outer sleeve of FIG. 5A;

FIG. 6A is a side view of a trocar punch assembly of the present invention comprising the trocar punch of FIGS. 4A-4B and the trocar outer sleeve of FIGS. 5A-5C; 6B is an end view of the trocar punch assembly of FIG. 6A along line 6B—6B of FIGS. 6A; and 6C is a cutaway view of the trocar punch assembly of FIG. 6A taken along section line 6C—6C of FIG. 6A.

FIG. 7A is a side cut-away view of a loading cartridge comprising a component of the apparatus of the preferred embodiment; FIG. 7B is an end view of the loading cartridge of FIG. 7A.

FIG. 8 is an exploded view of a cannula subassembly of the disclosed embodiment with some components thereof cut away to reveal interior detail.

FIG. 9 is a top view of a cannula hub of the cannula subassembly of FIG. 8.

FIG. 10 is an assembled view of the cannula subassembly of FIG. 8 partially cut away to reveal interior detail.

FIG. 11A is a side cutaway view of a cannula introducer according to the disclosed embodiment; FIG. 11B is a top view of the cannula introducer of FIG. 11A.

FIG. 12A is a side view depicting the cannula subassembly of FIG. 8 loaded onto the cannula introducer of FIGS. 11A; 12B is a top view of the assembly of FIG. 12A.

FIG. 13 is a side view of a cannula infusion assembly comprising the cannula subassembly of FIG. 8, loaded onto the cannula introducer of FIG. 11A.

FIG. 14A is a cutaway view of an inflatable prosthesis, in an uninflated state, which is implanted with the apparatus of the disclosed embodiment according to the method of the present invention; FIG. 14B is a cutaway view showing the inflatable prosthesis of FIG. 14A in an inflated condition.

Figure 1A:
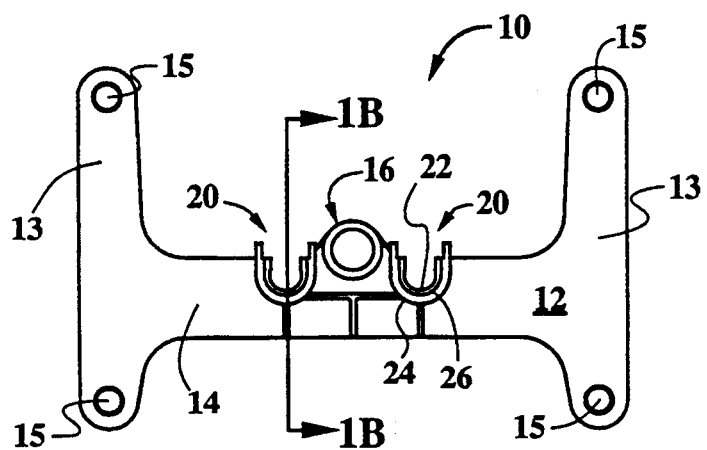
FIGS. 1A-1E illustrate a template comprising a component of a preferred embodiment of the present invention, where
Figure 1B:
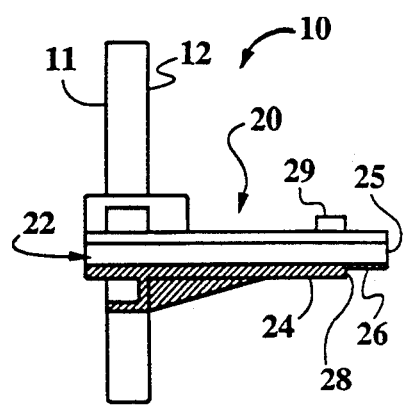
Figure 1C:
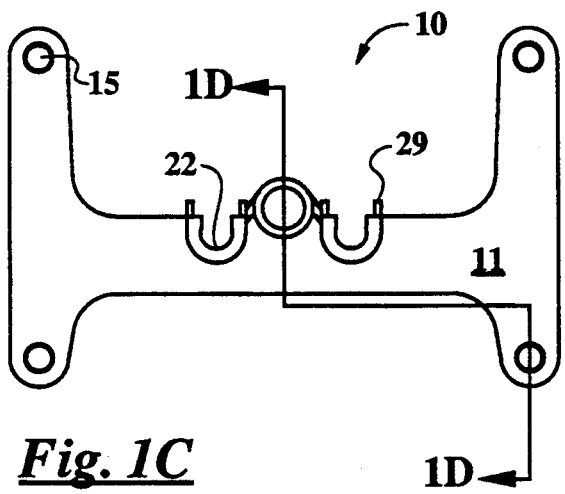
Figure 1D:
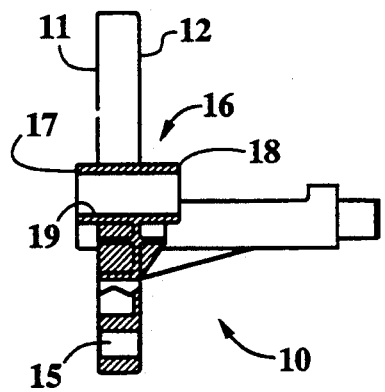
Figure 1E:
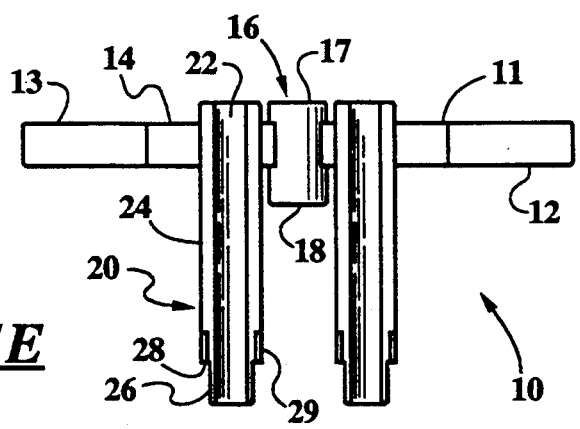
Figure 2A:
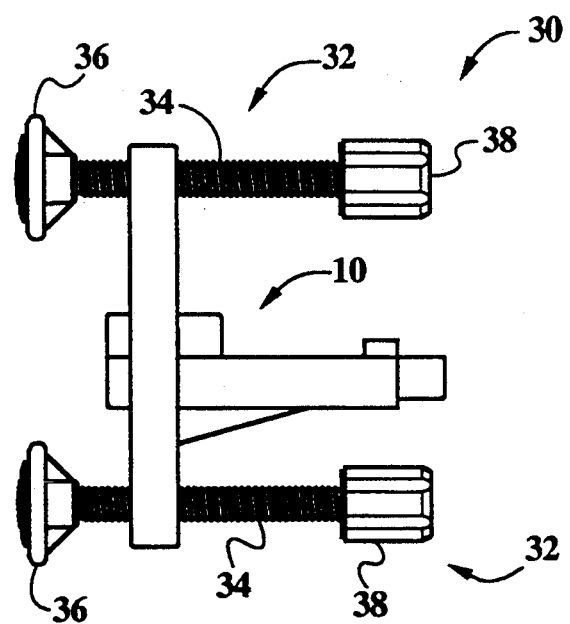
FIG. 2A is a side view of a template assembly comprising the template of FIGS. 1A-E; 2B is a side view of the template assembly of FIG. 2A partially cut away to reveal interior detail.

The method of the disclosed embodiment is shown in FIGS. 15–27, where:

FIG. 15 shows the assembly of a left-side catheter assembly of FIG. 3A with the template assembly of FIG. 2A, an identical right-side catheter assembly being omitted for clarity.

FIG. 16A is a side view of the assembled catheter assembly and template assembly of FIG. 15; FIG. 16B is a partial cutaway view of the assembly of FIG. 16A.

FIG. 17 is a side view of the catheter and template assembly of FIGS. 16A and 16B showing the catheter being inserted into the urethra of a patient.

FIG. 18 is a side view of the inserted catheter and template assembly of FIG. 17 showing the balloon of the catheter inflated to engage the bladder neck of the patient.

Figure 19A:
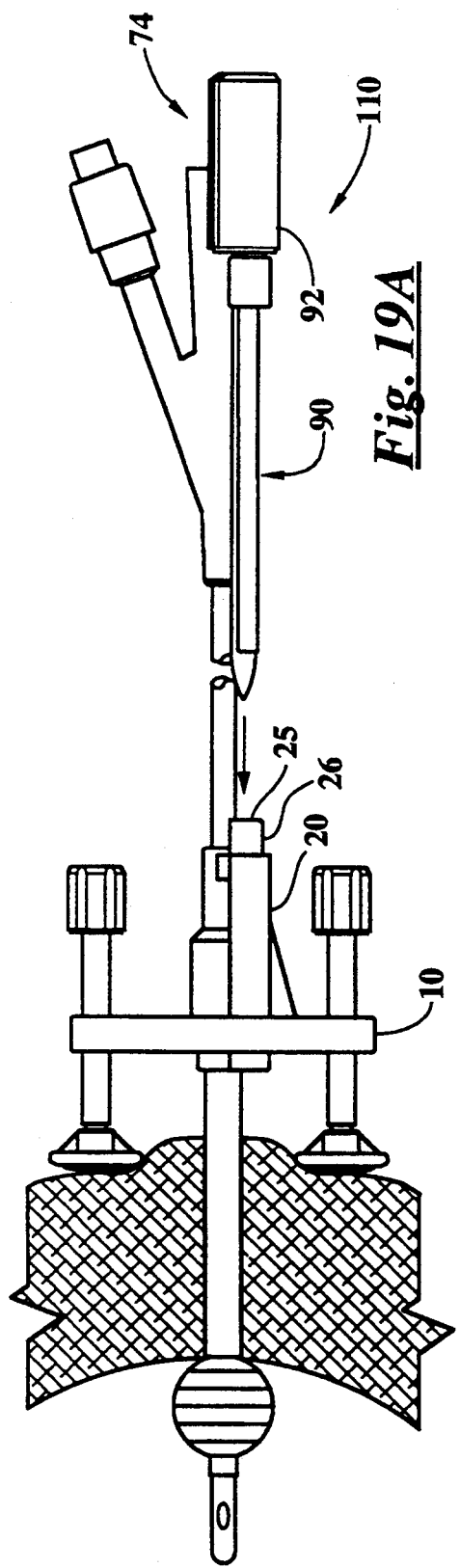
Figure 19B:
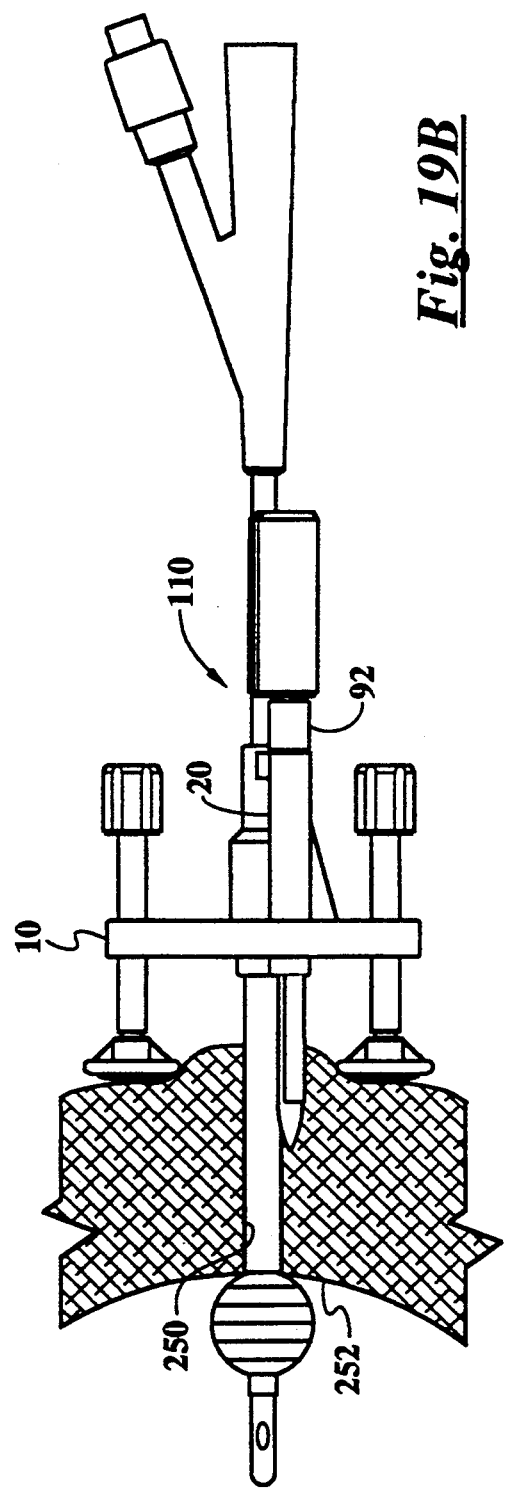

FIG. 19A is a side view of the inserted and inflated catheter and template assembly of FIG. 18 showing a left-side punch assembly of FIGS. 6A–C being inserted into a channel of the template, an identical right-side punch assembly being omitted for the sake of clarity; FIG. 19B shows the punch assembly inserted through the channel of the template and into the periurethral tissues of the patient; and FIG. 19C is a partial cutaway view of the assembly of FIG. 19B.

FIG. 20 is a side view of the inserted and inflated catheter and template assembly of FIGS. 19A–C showing the punch being withdrawn so as to leave the trocar outer sleeve engaged with the template assembly and having a portion thereof disposed within the periurethral tissues of the patient.

FIGS. 21A–D are side views depicting the sequence of steps by which the inflatable prosthesis of FIG. 14 is loaded onto a left-side cannula infusion assembly of FIG. 13, an identical right-side cannula infusion assembly and inflatable prosthesis being omitted for reasons of clarity.

Figure 22C:
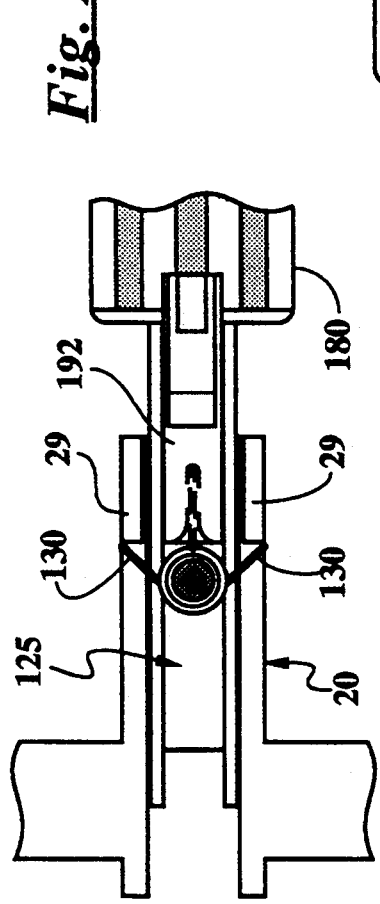

FIG. 22A is a side view of the cannula infusion assembly and associated inflatable prosthesis of FIG. 21D being inserted through the trocar outer sleeve of the assembly of FIG. 20 so as to position the inflatable prosthesis within the periurethral tissues of the patient; FIG. 22B is a side cutaway view of the assembly of FIG. 22A showing detail of the engagement between the cannula infusion assembly and the template assembly; and FIG. 22C is a partial top view of the assembly of FIG. 22A.

Figure 23:
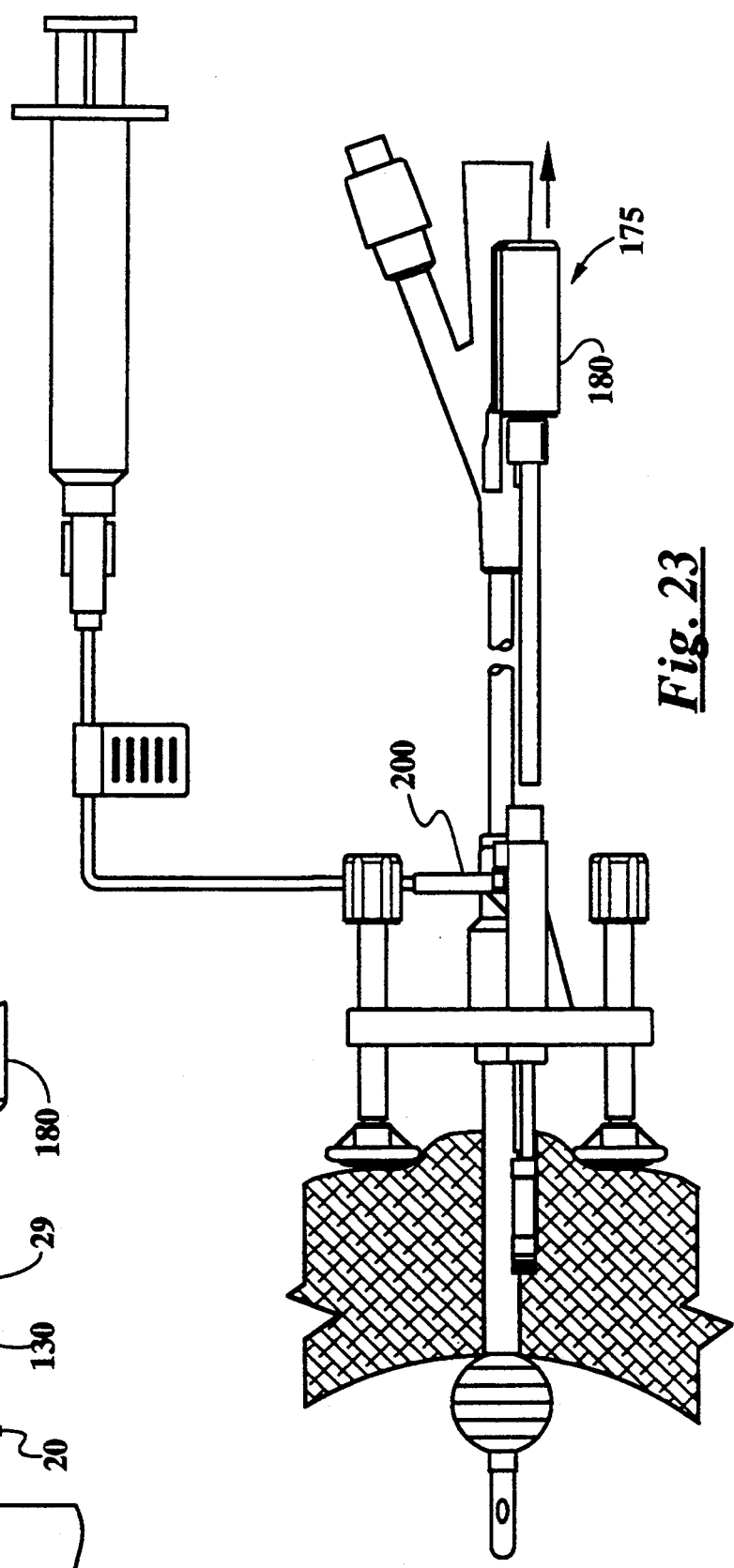

FIG. 23 depicts the withdrawal of the cannula introducer from the assembly of FIGS. 22A–C, leaving the cannula subassembly mounted to the template.

Figure 24:
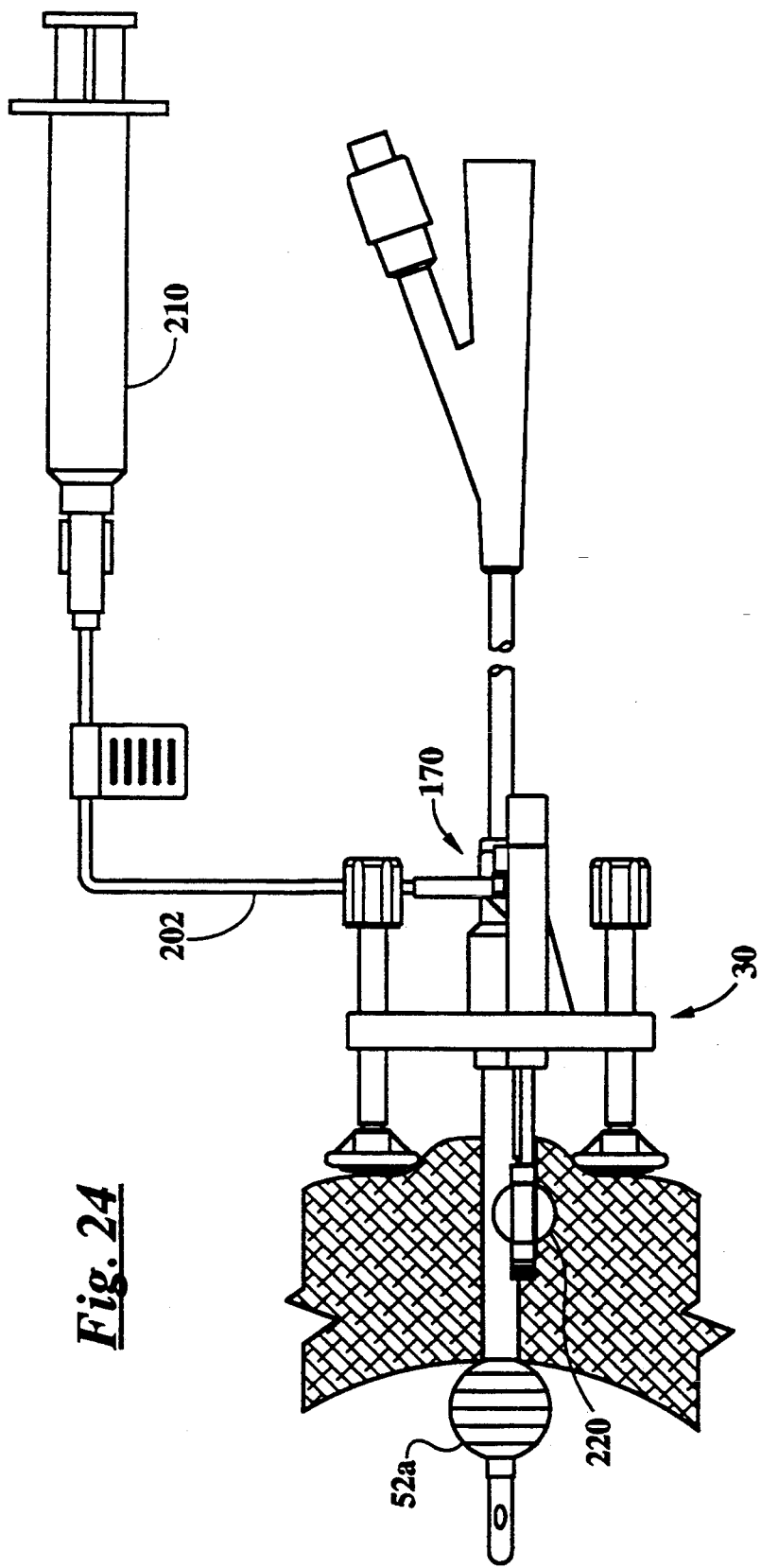

FIG. 24 shows the assembly of FIG. 23 with the prosthesis partially inflated within the periurethral tissues of the patient.

Figure 25:
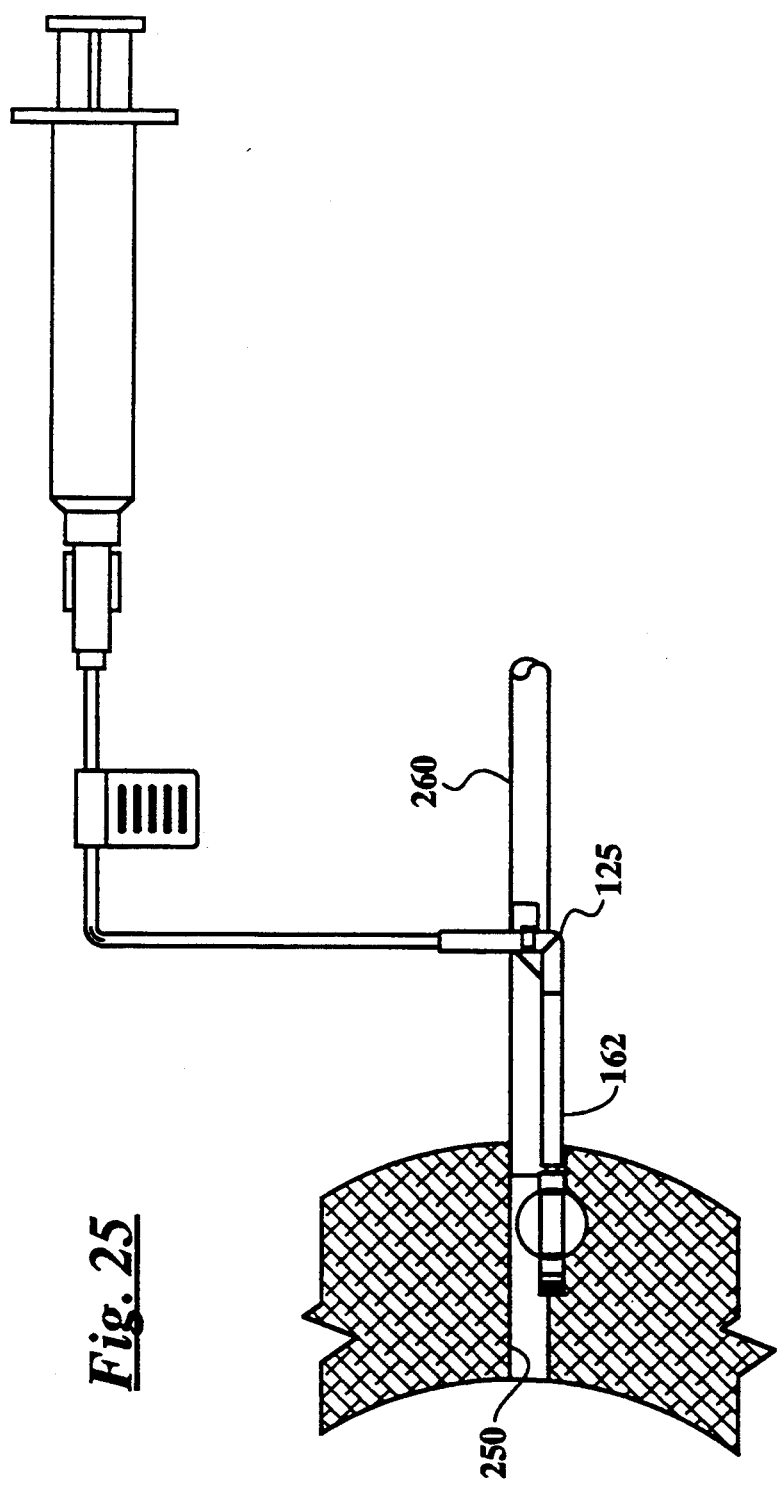

FIG. 25 shows the template assembly being disengaged, leaving the cannula subassembly and partially inflated prosthesis in place within the periurethral tissues of the patient, and a cystoscope being inserted into the urethra of the patient.

Figure 26:
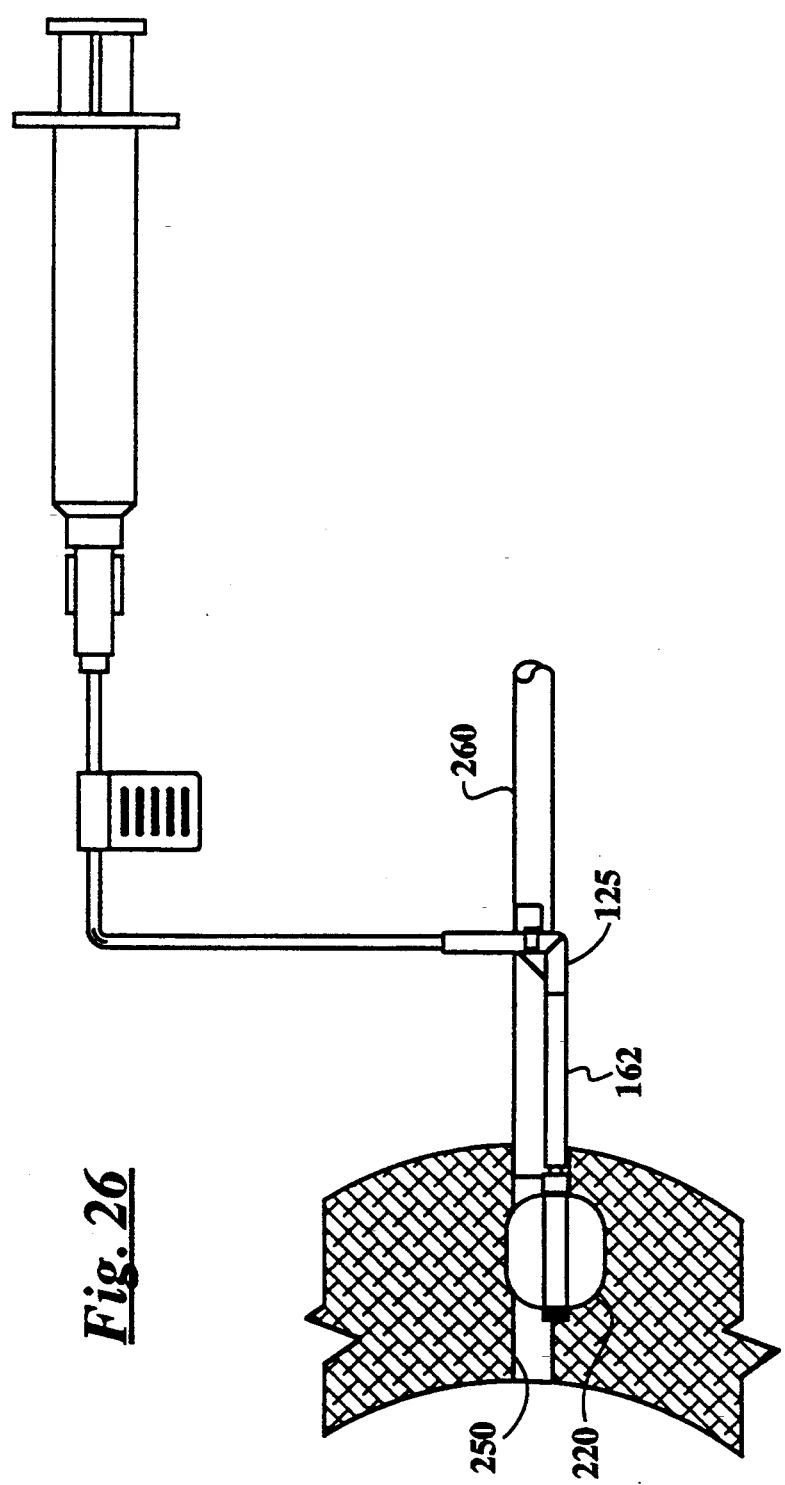

FIG. 26 shows the prosthesis being further inflated under cystoscopic guidance until the urethra coapts.

FIG. 27A shows the withdrawal of the cannula subassembly from the patient, leaving the inflated prosthesis implanted within the periurethral tissues of the patient; FIG. 27B is a partial cutaway view of the withdrawn cannula subassembly of FIG. 27A.

DETAILED DESCRIPTION OF THE DISCLOSED EMBODIMENT

Referring now in more detail to the drawings, in which like numerals indicate like elements throughout the several views, FIGS. 1A–1E illustrate a template which comprises a component of the guidance device of the disclosed embodiment. The template 10 is comprised of ABS plastic and is an essentially flat member comprising a front face 11 and a back face 12. The template 10 is essentially H-shaped, with two vertically extending arms 13 connected by a horizontal cross-member 14. Threaded bores 15 are formed through each of the arms 13 at their upper and lower ends.

The template 10 comprises a center guide tube 16 disposed at the center of the cross-member 14 and having an axis generally perpendicular to the plane of the back face 12. The center guide tube 16 comprises a proximal portion 17 extending from the front face 11 of the template and a distal portion 18 extending rearward from the back face 12 of the template. The inner wall 19 of the center guide tube 16 is essentially smooth.

Spaced outward and downward from the center guide tube 16 is an opposed pair of outer guide sleeves 20. Each outer guide sleeve 20 defines an upwardly opening U-shaped channel 22. A main portion 24 of each outer guide sleeve 20 extends rearward from the back face 12 of the template 10. Each outer guide sleeve terminates at a distal end 25. A portion of each center guide sleeve 20 adjacent its distal end 25 comprises a reduced section 26. The wall thickness of the reduced sections 26 is somewhat thinner than the thickness of the remainder of the outer guide sleeves 20 such that the outer dimensions of the reduced sections are somewhat smaller than the outer dimensions of the main guide sleeve portion 24 while the interior dimensions of the reduced sections 26 are equal to the interior dimensions of the main guide sleeve portions 24. A shoulder 28 is formed on each guide sleeve 20 at the junction between the main guide sleeve portion 24 and the reduced portion 26. Upwardly extending tabs 29 are formed at the upper edges of the main body portion 24 of each guide sleeve 20 just forward of the shoulder 28.

Figure 2B:
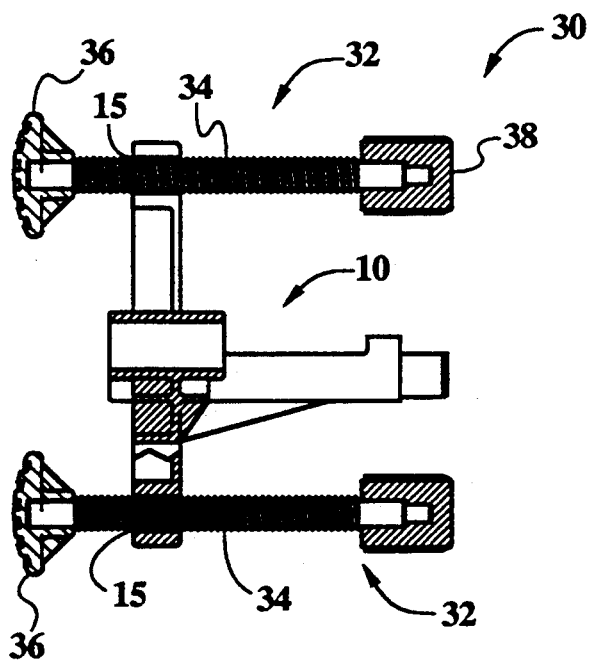

FIGS. 2A and 2B disclose a template assembly comprising 30 comprising the template 10 with adjustable leg assemblies 32 mounted thereto. Each adjustable leg assembly 32 comprises a threaded rod 34 having a foot pad 36 at its forward end and a thumb screw 38 at its rearward end. The threaded rod 34 of each leg assembly 30 is threaded into a corresponding one of the four threaded bores 15 formed in the corners of the template 10. In the disclosed embodiment the threaded rod 34 is comprised of nylon, the foot pad 36 and thumb screw 38 are molded from ABS plastic, and the foot pad and thumb screw are glued to opposing ends of the threaded rod after the rod has been threaded into the template 10.

FIGS. 3A and 3B show a positioning catheter assembly 40 comprising a positioning catheter 42, an obturator sleeve 44, an obturator sleeve collar 46, and a catheter collar 48. The positioning catheter 42 is a conventional 12 fr. silicone Foley catheter having a shaft 49, a proximal end 50 and a positioning catheter balloon 52 just rearward of the proximal end 50. The obturator sleeve 44 is a tubular member comprised of stainless steel and having an inner diameter approximately equal to the outer diameter of the catheter shaft 49. The obturator sleeve collar 46 is an annular collar comprised of ABS plastic and having an inner diameter equal to the outer diameter of the obturator sleeve 44. In the disclosed embodiment, the obturator sleeve collar 46 is glued onto one end of the obturator sleeve 44. However, it is also possible to form the obturator sleeve collar directly on the obturator sleeve such as by insert molding.

The catheter collar 48 is comprised of silicone and has a longitudinal opening of stepped diameter. At a first section 60 adjacent the forward end 62 of the catheter collar 48 the inner diameter of the catheter collar is somewhat larger than the outer diameter of the obturator sleeve 44, such that when the catheter collar 48 is positioned around the obturator sleeve 44, as shown in FIG. 3B, there is an annular space 63 between the obturator sleeve 44 and the forward end 62 of the catheter collar 48. More specifically, the inner diameter of the catheter collar 48 at the first section 60 is approximately equal to the outer diameter of the distal portion 18 of the center guide tube 16 of the template 10, and the annular space 63 between the obturator sleeve 44 and the forward end 62 of the catheter collar 48 is configured to receive the distal portion 18 of the template center guide tube therewithin.

Rearward of the first section 60 of the catheter collar 48 is a radially inwardly projecting flange 64. The inner diameter of the flange 64 is equal to the outer diameter of the obturator sleeve 44. Rearward of the flange 64 is a second section 66 having an inner diameter equal to the outer diameter of the obturator sleeve collar 46. Rearward of the second section 66 is a third second 68 having an inner diameter approximately equal to the outer diameter of the catheter shaft 49. The stepped transition between the second section 66 and the third section 68 defines a shoulder 69.

To assemble the positioning catheter assembly 40, the obturator sleeve collar 46 is glued to the distal end of the obturator sleeve 44. The catheter collar 48 is bonded to the catheter shaft 49 with a silicone adhesive or other suitable fastening arrangement. The proximal end 50 of the positioning catheter 42 is then inserted through the distal end of the obturator sleeve 44 and advanced until the obturator sleeve collar 46 enters the first section 60 of the catheter collar 48. As the positioning catheter 42 is advanced further, the obturator sleeve collar 46 advances past the inwardly extending annular flange 64 of the catheter collar 48 and into the third section 68 of the catheter collar. The shoulder 69 between the second and third sections 66, 68 of the catheter collar 48 serves as a positive stop to limit further advancement of the positioning catheter 42 with respect to the obturator sleeve 44. In this position, the inwardly extending annular flange 64 of the catheter collar 48 captures the obturator sleeve collar 46 and positively locks the positioning catheter 42 with respect to the obturator sleeve 44.

Referring now to FIGS. 4A and 4B, a trocar punch 74 comprises a shaft 76 and a trocar handle 78. The shaft 76 of the trocar punch 74 is comprised of stainless steel and has a sharpened proximal end 80. The trocar handle 78 is molded from ABS plastic and is secured to the distal end of the shaft 76 by insert molding, glue, or other suitable means. An annular recess 82 is formed at the forward end of the trocar handle 78 between an inner handle wall 84 and the shaft 76 of the punch 74. The annular recess 82 terminates in a base wall 86 at the rearward end of the recess. As shown in FIG. 4B, the inner wall 82 at the forward end of the trocar handle 78 has a pair of opposed, inwardly extending projections 88, the function and purpose of which will be explained below.

FIGS. 5A and 5B show a trocar outer sleeve 90. The trocar outer sleeve 90 is comprised of stainless steel and has a trocar outer sleeve adapter 92 secured to its distal end. The trocar outer sleeve adapter 92 is comprised of ABS plastic and is secured to the trocar outer sleeve 90 by insert molding, glue, or other suitable means. The trocar outer sleeve adapter 92 has a front end 93. A forward portion 94 of the trocar outer sleeve adapter 92 adjacent its front end 93 is U-shaped in cross-section, with walls circumscribing an arc of slightly greater than 180°. The inner wall 96 of the forward portion 94 of the trocar outer sleeve adapter 92 is spaced apart from the trocar outer sleeve 90 so as to form a recess 98 therebetween.

The distal portion 102 of the trocar outer sleeve adapter 92 has a smaller outer diameter than the forward portion 94. Like the forward portion 94, the distal portion 102 is essentially U-shaped in cross-section, each of the side walls of the distal portion terminating in an upper edge 104. At the lower edge of the rearward end 105 of the trocar outer sleeve adapter 92, a flange 106 is formed. The bottom surface 108 of the flange 106 is beveled downward and forward.

FIGS. 6A–6C disclose a trocar assembly 110 comprising a trocar punch 74 and a trocar outer sleeve 90. The shaft 76 of the trocar punch 74 is nested within the trocar outer sleeve 90, and the distal portion 102 of the trocar outer sleeve adapter 92 is received within the annular space 84 in the forward end 82 of the trocar handle 78. The rearward end 105 of the trocar outer sleeve adapter 92 abuts the base 84 of the annular recess 82 in the trocar handle 78. As shown in FIG. 6C, the upper edges 104 of the distal portion 102 of the trocar outer sleeve adapter 92 are captured beneath the projections 86 formed on the inner wall of the trocar handle 78 and thereby prevent relative rotation between the trocar punch 74 and the trocar outer sleeve 90. Also, because the U-shaped walls of the trocar outer sleeve 90 circumscribe an arc of greater than 180°, the shaft 76 of the trocar punch 74 is retained within the outer sleeve and thereby prevented from becoming laterally disengaged.

Referring now to FIG. 7, a loading cartridge 114 is illustrated. The loading cartridge 114 comprises a tubular body 116 which is closed at one end 118 and which has a tapered lead-in 120 at the other. The tubular body 116 of the loading cartridge 114 includes interior walls 124. In the disclosed embodiment, the loading cartridge 114 is comprised of styrene plastic. The purpose and function of the loading cartridge 114 will be explained below in conjunction with a discussion of the operation of the invention.

Referring now to FIGS. 8 and 9, a cannula hub 125 comprises an L-shaped body portion 126 comprised of ABS or other suitable material. As can perhaps best be seen in FIG. 9, the cannula hub 125 includes a rearwardly projecting fin 128 and a pair of wings 130 projecting outwardly and rearwardly at 45 degree angles to the fin 128. The cannula hub 125 includes a vertical bore 132 formed therein. As can be seen in FIG. 8, the vertical bore 132 includes an upper section 134 and a lower section 136 of smaller diameter than the upper section 134. A shoulder or step-down 138 is formed at the juncture between the upper and lower bore sections 134, 136. The vertical bore 134 communicates with a horizontal bore 140 comprising a forward bore section 142 and a rearward bore section 144 having a smaller diameter than the forward bore section 142. A shoulder 146 is formed at the juncture between the forward bore section 142 and the rearward bore section 144.

Also shown in FIG. 8 is a non-coring cannula needle 150 comprised of stainless steel. The cannula needle 150 comprises a shaft 151 and a sharpened forward end 152 which is angled with respect to the shaft 151 in the conventional manner to provide the non-coring feature. The shaft 151 further comprises a rearward end 153. A cannula needle sleeve 154 also comprised of stainless steel is bonded around the shaft 151 at the distal end 153 of the cannula needle 150, such as by an adhesive.

Further shown in FIG. 8 is a cannula tubing 156 having a forward end 157 and a rearward end 158. In the disclosed embodiment the cannula tubing 156 is comprised of polyurethane or other suitable material. A cannula tubing collar 160 comprised of ABS plastic or other suitable material is bonded onto the cannula tubing 156 adjacent the forward end 157 thereof. The inner diameter of the cannula tubing 156 corresponds to the outer diameter of the cannula needle sleeve 154, and the outer diameter of the cannula tubing 156 corresponds to the inner diameter of the forward section 142 of the horizontal bore 140 in the cannula hub 125.

Still referring to FIG. 8, a cannula release sleeve 162 is depicted. The cannula release sleeve 162 has a forward end 164 and a rearward end 166 and in the disclosed embodiment is comprised of stainless steel. The inner diameter of the cannula release sleeve 162 is slightly larger than the outer diameter of the cannula tubing collar 160. A cannula release sleeve bushing 168 comprised of ABS plastic is bonded to the inner wall 170 of the cannula release sleeve 162 at its rearward end 166. The inner diameter of the cannula release sleeve bushing 168 corresponds to the outer diameter of the cannula tubing 156 such that when the cannula tubing 156 is placed within the release sleeve bushing 168 a slight interference fit results.

FIG. 10 shows a cannula subassembly 170 comprising the cannula needle 150 with cannula needle sleeve 154, the cannula tubing 156 with cannula tubing collar 160, the cannula release sleeve 162 with cannula release sleeve bushing 168, and the cannula hub 125. To assemble the cannula subassembly 170, the rearward end 153 of the cannula needle 150 is inserted into the forward end 157 of the cannula tubing 156 and advanced until the cannula needle sleeve 154 bonded to the shaft 151 of the cannula needle 150 is snugly received within the forward end 157 of the cannula tubing 156. The rearward end 158 of the cannula tubing 156 is then inserted through the cannula release sleeve 162 from its forward end 164 until the rearward end 158 of the cannula tubing 156 extends from the rearward end 166 of the cannula release sleeve 162. The fit between the outer diameter of the cannula tubing collar 160 and the inner diameter of the cannula release sleeve 162 is such as will permit the cannula release sleeve 162 to slide freely in an axial direction. The fit between the outer diameter of the cannula tubing 156 and the inner diameter of the cannula release sleeve bushing 168 is such as will provide a slight interference fit between the cannula tubing 156 and cannula release sleeve bushing 168 but will permit the to slide in an axial direction upon exertion of a slight force. With the cannula tubing 156 and cannula release sleeve 162 thus assembled, the rearward end 158 of the cannula tubing 156 is inserted into the forward section 142 of the horizontal bore 140 in the cannula hub 125 and advanced until the distal end 158 of the cannula tubing 156 abuts the shoulder 146.

With the cannula subassembly 170 assembled in this manner, relative axial movement between the cannula tubing 156 and cannula release sleeve 162 is limited by the cannula release sleeve bushing 168 engaging the cannula tubing collar 160. In the disclosed embodiment the dimensions of the various components are configured such that when the cannula release sleeve 162 slides forward until the cannula release sleeve bushing 168 contacts the cannula tubing collar 160, the cannula needle 150 is completely contained within the cannula release sleeve 162.

FIGS. 11A and 11B illustrate a cannula introducer 175 comprising a cannula outer sleeve 178 and a cannula handle 180. The cannula outer sleeve 178 is a tubular member having its upper portion removed at its forward end 182 to form a U-shaped channel 184. The walls of the U-shaped channel 184 circumscribe an arc of slightly greater than 180° such that the width of the opening at the upper end of the channel is narrower than the diameter of the cannula outer sleeve 178. The dimensions of the cannula outer sleeve 178 are such that the cannula subassembly 170 can be slidably received within the U-shaped channel portion 184 at the forward end of the cannula introducer 175 but cannot fit through the opening at the upper end of the U-shaped channel, whereby the cannula subassembly 170 is captured laterally within the cannula introducer 175.

The cannula handle 180 includes inner walls 186 at its forward end 188 which are spaced apart from the cannula outer sleeve 178 to form a recess therebetween. A snap detail 190 is formed at the lower end of the cannula handle to project into the recess. At the upper end of the cannula handle 180 a tongue 192 projects forwardly. The tongue 192 has a longitudinally extending channel 194 formed in its lower face.

FIGS. 12A and 12B show the cannula subassembly 170 mounted to the cannula introducer 175. The fin 128 of the cannula hub 125 is received within the channel 194 in the lower face of the tongue 192 of the cannula handle 180. The cannula release sleeve 162 and cannula tubing 156 reside within the U-shaped channel 184 in the forward end of the cannula outer sleeve 178 with only the forward end 152 of the cannula needle 150 extending beyond the forward end of the cannula introducer 175.

FIG. 13 shows a cannula infusion assembly 200 loaded onto the cannula introducer 175. The cannula infusion subassembly comprises the cannula subassembly 170 having an infusion line 202 inserted into the upper end 134 of the vertical bore 132 in the cannula hub 125. The infusion line 202 is comprised of a thermoplastic elastomer and has an outer diameter which fits snugly within the upper section 134 of the vertical bore 132. The forward end of the infusion line 202 is inserted into the upper bore section 134 and advanced until the forward end of the infusion line engages the shoulder 138. An infusion line restraint pad 204 is mounted to the infusion line and provides strain relief, as will be explained below. The rearward end of the infusion line 202 is connected by a luer adapter 208 to a 3 cc syringe 210 of conventional design.

An inflatable prosthesis 220 of a type intended for implantation within periurethral tissues is shown in FIGS. 14A and B. The prosthesis 220 is of a type well known to those skilled in the art and hence will be described herein only briefly. The prosthesis 220 of the disclosed embodiment is sold by the Bard Urological Division, Covington, Ga., U.S.A., under the trademark Genisphere ®. The inflatable prosthesis 220 includes a needle guide 222 having a port 223 formed therein. An elastomeric inner housing 224 snugly surrounds the needle guide 222 and includes a hole 225. An elastomeric balloon 228 is disposed around the inner housing 224. To inflate the prosthesis 220, the tip of a catheter or other suitable instrument is inserted into the needle guide 222. Fluid is infused under slight pressure through the catheter and into the needle guide, from where it passes through the port 223. The fluid slightly distends the inner housing 224 and flows into the resulting space between the needle guide 222 and the inner housing 224, finally passing through the hole 225 and causing the outer balloon 228 to inflate. When fluid pressure within the catheter is released, the inner housing 224 returns to its contracted state in snug engagement with the needle guide 222, thereby preventing the return flow of fluid from the balloon and thus serving as a check valve.

The use of the apparatus of the present invention to direct a hypodermic instrument to a predetermined target location without the periurethral tissues is illustrated beginning with FIG. 15. The positioning catheter assembly 40 is assembled to the template assembly 30 by inserting the proximal end 50 of the positioning catheter 42 through the center guide tube 16 of the template 10. The positioning catheter 42 is advanced through the center guide tube 16 until the annular space 63 at the forward end 62 of the catheter collar 48 advances over the distal portion 18 of the center guide tube 16, as shown in FIG. 16A. The positioning catheter assembly 40 is properly positioned with respect to the template assembly 30 when the annular shoulder 64 of the catheter collar 48 abuts the distal end 18 of the center guide tube 16, as shown in FIG. 16B. The positioning catheter assembly 40 is held in position with respect to the template assembly 30 by a friction fit between the first section 60 of the catheter collar 48 and the distal portion 18 of the center guide tube 16. With the positioning catheter assembly 40 thus mounted to the template assembly 30, the proximal end 50 of the positioning catheter 42 projects forward from the front face 11 of the template 10.

With the positioning catheter assembly 40 thus assembled to the template assembly 30, the proximal end 50 of the positioning catheter 42 is advanced through the patient's urethra 250, as shown in FIG. 17, until the proximal end 50 of the positioning catheter 42 resides within the bladder neck 252. The catheter balloon 52 is then inflated in the conventional manner, and the positioning catheter assembly 40 and template assembly 30 are drawn outwardly until the inflated balloon 52a is firmly seated against the bladder neck, as shown in FIG. 18. The four adjustable leg assemblies 32 of the template assembly 30 are then extended by turning the thumb screws 38 to extend the leg assemblies until the pads 36 bear against the patient's abdomen 254. In the disclosed embodiment, the upper pair of leg assemblies 32 bear against the patient's pubic bone, and the lower pair of leg assemblies 32 bears against the pelvic bone. The adjustable leg assemblies 32 thereby exert a constant tension on the positioning catheter 42 and maintain the template 10 at a predetermined distance from the bladder neck 252.

Referring now to FIGS. 19A–C, the two trocar assemblies 110 each comprising a trocar punch 74 and a trocar outer sleeve 90 are introduced through the outer guide sleeves 20 of the template 10. The trocar assemblies 110 are advanced through the periurethral tissues until the trocar outer sleeve adapter 92 engages the reduced rear portion 26 of the center guide sleeve 20. As illustrated more specifically in FIG. 19C, the reduced rear portion 26 of the outer guide sleeve 20 is received within the recess 98 formed between the inner wall 96 of the forward portion 94 of the trocar outer sleeve adapter 92 and the trocar outer sleeve 90. The forward end 93 of the trocar outer sleeve adapter 92 engages the shoulder 28 on the outer guide sleeve 20 and serves as a positive stop to limit the depth of penetration of the trocar punch 74. Because the template 10 is fixed in predetermined spaced relation with respect to the bladder neck 252, the tracts formed by advancing the trocar punches 74 are properly positioned with respect to the bladder neck 252 and urethra 250.

Referring now to FIG. 20, the trocar punches 74 are withdrawn from their respective trocar outer sleeves 90, leaving the trocar outer sleeves 90 in place in the periurethral tissues 256 on either side of the urethra to define a pair of working channels.

FIGS. 21A–D illustrate the loading of the inflatable prostheses 220 onto the cannula infusion assemblies 200. Referring first to FIG. 21A, a prosthesis 220 is inserted into a loading cartridge 114. The interior walls 124 of the loading cartridge 114 center the prosthesis 220 within the cartridge. As shown in FIGS. 21B, the cannula infusion assemblies 200 are loaded onto their respective cannula introducers 175. The cannula needle 150 of the cannula infusion assembly 200 is then inserted into the loading cartridge 114 as illustrated in FIG. 21C until the sharpened forward end 152 of the cannula needle 150 penetrates the core of the prosthesis 220. The cannula infusion assembly 200 and cannula introducer 175 are then withdrawn from the loading cartridge 114, the prosthesis 220 being retained on the end of the cannula needle 150. The second cannula infusion assembly 200 is then loaded with a prosthesis 220 in the same manner.

Referring now to FIG. 22A, the cannula infusion assemblies 200 and cannula introducers 175 are inserted into the rearward end 105 of the trocar outer sleeve adapter 92 and advanced through the periurethral tissues. As shown in FIG. 22B, as the cannula handle 78 advances over the trocar outer sleeve adapter 92, the snap detail 190 of the cannula handle 180 advances past the flange 106 of the trocar outer sleeve adapter 94 to latch the cannula introducer 175 onto the trocar outer sleeve adapter 92. Simultaneously, the wings 130 projecting outwardly and rearwardly from the cannula hub 125 advance past the tabs 29 extending upwardly from the guide sleeve 20 and snap into place behind the tabs, as shown in FIG. 22C. The infusion lines 202 are strain relieved by clamping the infusion line restraint pads 204 to the patient's surgical drape (not shown). At this point both of the cannula infusion assemblies 200 and cannula introducers 175 are inserted into their respective trocar outer sleeve adapters 92.

Referring now to FIG. 23, with the cannula infusion assemblies 200 mechanically engaged within their respective template outer guide sleeves 20, the physician grasps each cannula handle 180 and withdraws the cannula introducers 175. Since the snap detail 190 of each cannula handle 180 is mechanically engaged with the flange 106 of the respective trocar outer sleeve adapter 92, the trocar outer sleeves 90 are withdrawn along with the cannula introducers 175. As the cannula introducers 175 and trocar outer sleeve adapters 92 are withdrawn, the infusion assemblies 200 are retained within their respective guide sleeves 20 by the wings 130 of the cannula hubs 125 confronting the tabs 29 projecting from the guide sleeves 20. Thus when the cannula introducers 175 and trocar outer sleeve adapters 92 are withdrawn, the infusion assemblies 200 remain engaged with the template 10.

When the cannula introducers 175 and trocar outer sleeve adapters 92 have been withdrawn, each prosthesis 220 is partially inflated as shown in FIG. 24 by infusing 1.0 cc of sterile saline from the syringe 210 through the infusion line 202 and hence through the cannula subassembly 170. This partial inflation of the prosthesis 220 tentatively anchors the prosthesis at its implant position within the periurethral tissues 256. The positioning catheter 42 is then deflated and withdrawn from the urethra 250, thereby allowing for a cystoscope 260 to be inserted into the urethra as shown in FIG. 25 to monitor the coaptation effects of the inflatable prostheses 220. The template assembly 30 may also be removed, leaving the cannula subassemblies 170 in place. To remove the template assembly 30, the physician displaces the template 10 downward, disengaging the template from the cannula subassemblies 170 through the openings in the U-shaped outer guide sleeves 20. Then, while the physician cystoscopically monitors the urethra, the prostheses 220 are concurrently inflated with up to 3.0 cc of sterile saline as shown in FIG. 26, causing the urethra 250 to coapt.

At this juncture, the physician may wish to perform urodynamic tests to insure that sufficient pressure is exerted on the urethra to achieve continence. Depending upon the results of the test, inflation of the prostheses 220 may require adjustment to obtain the desired result.

When the physician is satisfied with the extent of pressure exerted by the prostheses, the cannula subassemblies 170 may be withdrawn from the patient. Referring now to FIGS. 27A-B, with the prostheses 220 inflated within the periurethral tissues 256, the physician grasps the cannula release sleeve 162 and holds it in place while withdrawing the cannula hub 125 with the other hand. This relative movement between the cannula release sleeve 162 and the cannula hub 125 accomplishes to purposes. First, since the body of the prosthesis 220 is larger than the diameter of the cannula release sleeve 162, the prosthesis is prevented from moving outwardly as the cannula needle 150 is withdrawn. The cannula needle 150 is thus extracted from the prosthesis 220. Second, the relative movement retracts the cannula needle 150 within the cannula release sleeve 162 so as to protect the user against accidental needle sticks, and the slight friction fit between the cannula release sleeve bushing 168 and the cannula tubing 156 maintains the cannula release sleeve in this extended position. The cannula release sleeve 162 is fully extended with respect to the cannula hub 125 when the cannula release sleeve bushing 168 engages the cannula tubing collar 160, preventing the cannula release sleeve 162 from becoming disengaged from the cannula needle sleeve 154.

Withdrawal of the cannula subassembly 170 from the patient completes the procedure.

One feature of the present invention is the provision of a template assembly 30 which, when firmly mounted to the patient, supports and directs the various instruments for forming the working tracts, implanting the prostheses within the working tracts, and inflating the prostheses so as to coapt the urethra. An advantage of this feature is that a complex procedure involving forming multiple working tracts, implanting multiple prostheses, and inflating the prostheses under cystoscopic monitoring, can be carried out by a single physician. Since the template assembly 30 supports the various instruments, the physician can release the instruments to perform another.

Another feature of the disclosed embodiment is the provision of a means for properly positioning the inflatable prostheses along the length of the urethra. It has been found that regardless of the length of the patient's urethra, the urethral sphincter is always positioned at approximately the same position relative to the bladder neck. More particularly, irrespective of the length of the urethra, the urethral sphincter is disposed approximately 1 cm from the bladder neck. Accordingly, by configuring the cannula subassembly 170 such that the inflatable prosthesis 220 extends forward of the front face 11 of the template 10 by a distance 1 cm less than the distance between the front face of the template and the trailing edge of the balloon 52 of the positioning catheter 42, the depth of penetration of the cannula subassembly will be controlled, and the prosthesis will always be properly located along the length of the urethra so as to be properly positioned to coapt the tissues adjacent the sphincter.

A further feature of the disclosed embodiment is the provision of a means for controlling the depth of penetration of the introducing instruments. Because the trocar punch 74 and cannula subassembly 170 are positively limited by the template 10 from advancing beyond a predetermined depth, the risk of such introducing instruments accidentally overpenetrating and puncturing the bladder or other organ or vessel lying beyond the target location is eliminated.

Still another feature of the disclosed embodiment is the provision of a means for forming a tract within the periurethral tissues which is parallel to the urethra and in predetermined spaced relation thereto. One advantage of this feature is that, because the catheter locates and fixes the urethra, and because the template defines a pair of axes which are parallel to the axis of the catheter and in predetermined spaced relation thereto, the working channels defined by the template are also parallel to the urethra and in predetermined spaced relation thereto. Further, because the axes of the tracts are spaced apart from the axis of the catheter by the same distance by which the uninflated prosthesis should be spaced from the urethra, the physician using the apparatus of the present invention is always assured that the inflatable prostheses will not be positioned too close or too far from the urethra.

A further advantage of the feature of defining working tracts parallel to the urethra is that since by definition a parallel tracts will never intersect the urethra, it is impossible for the physician accidentally to lacerate or to puncture the urethra during the implantation procedure.

In one aspect the method and apparatus of the present invention provides a means for properly positioning a pair of prostheses in such a manner that the implantation of the first prosthesis does not adversely affect the positioning of the second prosthesis. According to prior art methods, when the first prosthesis is implanted within the periurethral tissues and inflated, the pressure exerted by the prosthesis can displace the urethra from its normal alignment. Then, because the urethra is not in its normal position, the physician can have difficulty in properly locating the second prosthesis with respect to the urethra. According to one aspect of the present invention, however, two steps are taken to minimize this problem. First, the positioning catheter 42 maintains the urethra in its proper alignment throughout the procedure and until both prostheses 220 are inflated. In addition, both prostheses 220 are implanted at their target locations within the periurethral tissues before either prosthesis is inflated. Thus the effects of the urethra being displaced by the inflation of only one prosthesis 220 are substantially eliminated.

The preferred embodiment has been disclosed with respect to a template 10 which defines a pair of axes which are parallel to the axis defined by the catheter collar 16.

Consequently, the template 10 defines a pair of working channels which are parallel to the urethra. However, it will be appreciated that suitable results may also be obtained by a template which defines working channels which terminate at the predetermined target location but which are not parallel to the urethra. By limiting the depth of penetration along a nonparallel path, the template can still ensure that the hypodermic instrument reaches the target location within the periurethral tissues without puncturing the urethra or bladder neck.

It will also be appreciated that the template apparatus of the present invention may be used for purposes other than implanting inflatable prostheses. For example, the template could be used for directing the tip of a hypodermic needle along a line and to a depth corresponding to a target location within the periurethral tissues. A hypodermic needle thus directed could be used, for example, to inject polymers, biopolymers, or the like directly into the periurethral tissues to increase the localized tissue volume in the vicinity of the urethral sphincter. Other purposes for this apparatus will be readily appreciated those skilled in the art.

Finally, it will be understood that the preferred embodiment has been disclosed by way of example, and that other modifications may occur to those skilled in the art without departing from the scope and spirit of the appended claims.

What is claimed is:

1. A method for effecting coaptation of a urethra of a patient, comprising the steps of:
    forming a first working channel through the periurethral tissues of said patient to a first target location in predetermined relation to said urethra;
    forming a second working channel through the periurethral tissues of said patient to a second target location in predetermined relation to said urethra and to said first target location;
    introducing a first inflatable prosthesis through said first working channel to said first target location;
    introducing a second inflatable prosthesis through said second working channel to said second target location;
    subsequent to said step of forming said second working channel, inflating said first inflatable prosthesis; and
    inflating said second inflatable prosthesis, said first and second prostheses being inflated such that coaptation of said urethra results.

2. The method of claim 1, comprising the further step of placing said urethra in predetermined alignment prior to forming either of said first and second working channels.

3. The method of claim 2, wherein said step of placing said urethra in predetermined alignment comprises the step of inserting a substantially rigid catheter of predetermined configuration into said urethra so as to cause said urethra to assume said predetermined configuration.

4. The method of claim 1, wherein said step of inflating said first inflatable prosthesis subsequent to said step of forming said second working channel comprises the step of inflating said first inflatable prosthesis subsequent to said step of introducing said second inflatable prosthesis through said second working channel to said second target location.

5. The method of claim 1, comprising the further step, prior to inflation of either of said first and second prostheses, of inserting a cystoscope into said urethra for visualization of said urethra as said first and second prostheses are inflated, whereby coaptation of said urethra can be visually monitored.

* * * * *